(12) United States Patent
Hinner

(10) Patent No.: US 11,382,963 B2
(45) Date of Patent: Jul. 12, 2022

(54) ENGINEERED T CELLS AND USES THEREFOR

(71) Applicant: Pieris Pharmaceuticals GmbH, Freising-Weihenstephan (DE)

(72) Inventor: Marlon Hinner, Munich (DE)

(73) Assignee: Pieris Pharmaceuticals GmbH, Freising-Weihensteph (DE)

( * ) Notice: Subject to any disclaimer, the term of this patent is extended or adjusted under 35 U.S.C. 154(b) by 961 days.

(21) Appl. No.: 15/542,915

(22) PCT Filed: Jan. 11, 2016

(86) PCT No.: PCT/EP2016/050326
§ 371 (c)(1),
(2) Date: Jul. 11, 2017

(87) PCT Pub. No.: WO2016/113203
PCT Pub. Date: Jul. 21, 2016

(65) Prior Publication Data
US 2018/0021418 A1    Jan. 25, 2018

(30) Foreign Application Priority Data
Jan. 12, 2015   (EP) .................................... 15000047

(51) Int. Cl.
| | |
|---|---|
| *A61K 39/00* | (2006.01) |
| *C07K 14/705* | (2006.01) |
| *C12N 5/0783* | (2010.01) |
| *C07K 14/725* | (2006.01) |
| *C07K 14/47* | (2006.01) |
| *C07K 14/54* | (2006.01) |

(52) U.S. Cl.
CPC .......... *A61K 39/0011* (2013.01); *C07K 14/47* (2013.01); *C07K 14/5434* (2013.01); *C07K 14/705* (2013.01); *C07K 14/7051* (2013.01); *C07K 14/70521* (2013.01); *C07K 14/70596* (2013.01); *C12N 5/0636* (2013.01); *A61K 2039/5156* (2013.01); *A61K 2039/5158* (2013.01); *C07K 2317/622* (2013.01); *C07K 2318/20* (2013.01); *C07K 2319/02* (2013.01); *C07K 2319/03* (2013.01); *C07K 2319/22* (2013.01); *C07K 2319/30* (2013.01); *C07K 2319/33* (2013.01); *C07K 2319/74* (2013.01); *C12N 2510/00* (2013.01)

(58) Field of Classification Search
CPC ........ A61K 39/0011; A61K 2039/5156; A61K 2039/5158; C07K 14/47; C07K 14/5434; C07K 14/705; C07K 14/7051; C07K 14/70521; C07K 14/70575; C07K 14/775; C07K 14/70596; C07K 2317/622; C07K 2318/20; C07K 2319/02; C07K 2319/03; C07K 2319/22; C07K 2319/30; C07K 2319/33; C07K 2319/74; C12N 5/0636; C12N 2510/00
See application file for complete search history.

(56) References Cited

U.S. PATENT DOCUMENTS

| | | | | |
|---|---|---|---|---|
| 7,892,827 B2 * | 2/2011 | Matschiner | ............. | A61P 31/00 435/325 |
| 9,221,885 B2 * | 12/2015 | Matschiner | ............. | C07K 14/47 |
| 9,745,368 B2 * | 8/2017 | Milone | ............. | C07K 14/70535 |
| 2009/0305963 A1 * | 12/2009 | Sukhatme | ............. | A61K 38/164 514/15.1 |
| 2009/0305982 A1 | 12/2009 | Jensen et al. | | |
| 2011/0098211 A1 * | 4/2011 | Matschiner | ............. | A61P 35/00 514/1.2 |

FOREIGN PATENT DOCUMENTS

| | | | | |
|---|---|---|---|---|
| WO | WO-2005/019256 A2 | 3/2005 | | |
| WO | WO-2006/056464 A2 | 6/2006 | | |
| WO | WO-2008/015239 A2 | 2/2008 | | |
| WO | WO-2011154420 A2 * | 12/2011 | ............. | A61P 31/04 |
| WO | WO-2012065978 A1 * | 5/2012 | ............. | A61P 35/00 |
| WO | WO-2012/072806 A1 | 6/2012 | | |
| WO | WO-2012072806 A1 * | 6/2012 | ............. | C07K 14/47 |
| WO | WO-2012/136685 A1 | 10/2012 | | |
| WO | WO-2013/174783 A1 | 11/2013 | | |
| WO | WO-2014/145252 A2 | 9/2014 | | |
| WO | WO-2014/153114 A1 | 9/2014 | | |
| WO | WO-2014/153270 A1 | 9/2014 | | |

OTHER PUBLICATIONS

Chmielewski et al., Cancer Immunol Immunother 61:1269-1277 (Year: 2012).*
Lloyd et al., Protein Engineering, Design & Selection 22:159-168 (Year: 2009).*
Edwards et al., J Mol Biol.334(1): 103-118 (Year: 2003).*
Skerra et al., Reviews in Molecular Biotechnology 74: 257-275 (Year: 2001).*
Chmielewski et al. "Of CARs and TRUCKs: chimeric antigen receptor (CAR) T cells engineered with an inducible cytokine to modulate the tumor stroma", Immunological Reviews, vol. 258, 2014, pp. 83-90.

(Continued)

*Primary Examiner* — Phuong Huynh
(74) *Attorney, Agent, or Firm* — Neal, Gerber & Eisenberg LLP

(57) ABSTRACT

Lipocalin muteins specific to a predetermined antigen can be transduced into a T cell to bring therapeutic benefits to patients in need. In one example, a lipocalin mutein specific to a predetermined antigen (e.g., a target differentially expressed on the surface of a tumor cell) can be transduced into a T cell membrane to serve as an antigen receptor, offering benefits over conventionally deployed antibody-derived protein moieties such as a single chain variable fragment (scFv). Benefits include a more stable structure, leading to superior target engagement, for example. Further, lipocalin muteins specific to a predetermined antigen (e.g. an immunomodulatory target such as an immune checkpoint or costimulatory molecule) can be transduced into a T cell for secretion thereby, bringing an added therapeutic benefit. Specific examples of such modified T cells and methods of making and using the same are provided herein.

Figure 1:
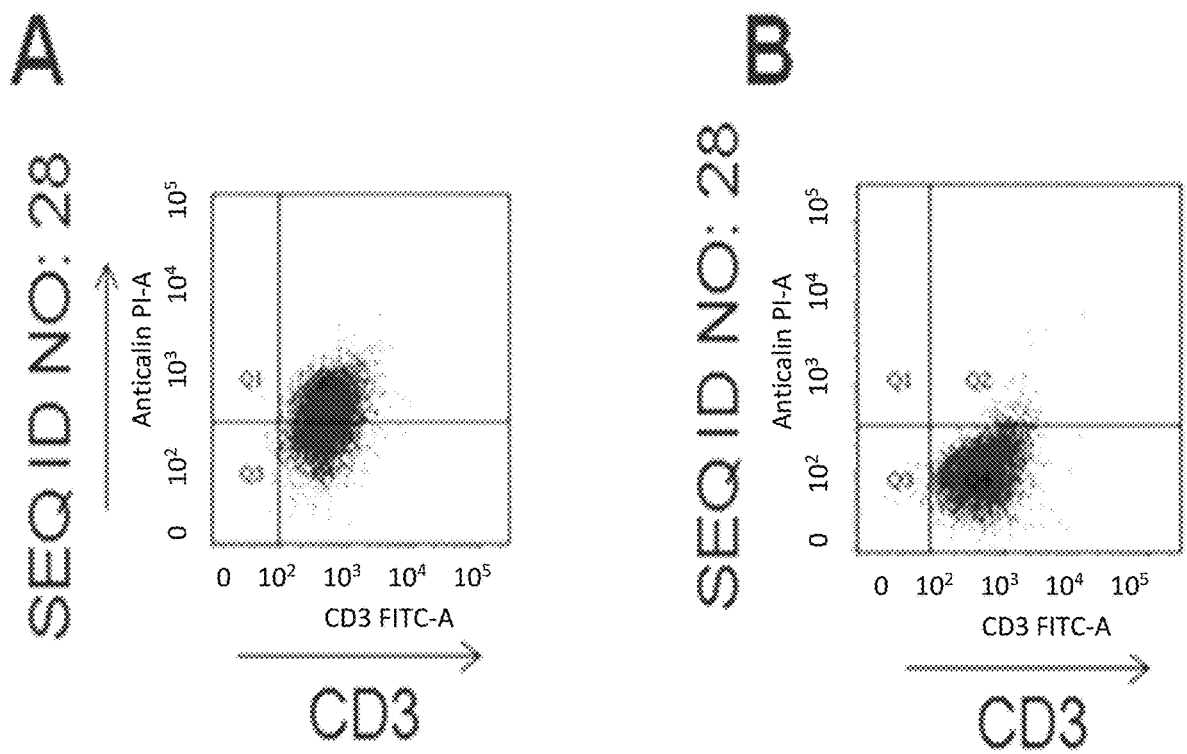

5 Claims, 3 Drawing Sheets
Specification includes a Sequence Listing.

(56) References Cited

OTHER PUBLICATIONS

Chmielewski et al., "CAR T cells transform to trucks: chimeric antigen receptor-redirected T cells engineered to deliver inducible IL-12 modulate the tumour stroma to combat cancer," Cancer Immunology Immunotherapy, vol. 61, 2012, pp. 1269-1277.
International Search Report and Written Opinion issued in corresponding application No. PCT/EP2016/050326 dated Apr. 28, 2016.
Pegram, H. et al., Blocking CD47 Improves CAR T Cell, Molecular Therapy, 22(1):S297 (2014).
Schonfeld, D. et al., An engineered lipocalin specific for CTLA-4 reveals a combining site with structural and conformational features similar to antibodies, PNAS, 106(20):8198-1203 (2009).

* cited by examiner

ENGINEERED T CELLS AND USES THEREFOR

CROSS-REFERENCE TO RELATED APPLICATIONS

This application is a National Stage application of PCT/EP2016/050326, filed Jan. 11, 2016, which claims priority from European application EP 15000047.9, filed Jan. 12, 2015.

BACKGROUND

T-cells transduced with artificial chimeric antigen receptors (CARs), also called CAR-T cells, are being deployed for the treatment of cancer (Shi et al. 2014). The CAR-T approach has provided positive clinical results in hematologic cancers such as acute lymphoblastic leukemia (ALL) and chronic lymphocytic leukemia (CLL). In a recent trial, for example, 30 patients with relapsed or refractory ALL were infused with autologous T cells transduced with the CD19-directed chimeric antigen receptor CTL019 (formerly called CART-19). Of these, 27 patients (90%) achieved complete remission (Maude et al. 2014). Sustained remission was achieved with a 6-month event-free survival rate of 67% and an overall survival rate of 78%.

CARs are transmembrane proteins stably anchored in the T-cell plasma membrane. A CAR is an artificial fusion of multiple parts: the extracellular part consists of a recognition domain binding to a cancer cell target; the intracellular part contains the signaling domain(s) of one or more (co-)stimulatory immunoreceptors; and the two are fused via a linker- and transmembrane domain. In the case of CTL019, for example, the recognition domain is an antibody single chain fragment (scFv) specific for CD19, the linker- and transmembrane regions are grafted from the membrane protein CD8, and the intracellular signaling part consists of the complete intracellular domains of CD137 and CD3zeta fused in tandem. When a T-cell transduced with this construct encounters a CD19-positive target cell, the chimeric antigen receptor is clustered, which results in activation of the signaling pathways downstream of CD3zeta and of the costimulatory receptor CD137, in turn leading to activation of T-cell proliferation, cytokine secretion, survival and the capacity to kill.

With this design, CTL019 is an example for a "second generation" CAR, identified by the presence of two immunostimulatory domains. In contrast, "first generation" CARs contain only a single immunostimulatory domain—usually that of CD3zeta—while in "third generation" CARs, overall three intracellular immunostimulatory domains are fused in tandem, for example those of CD3zeta, CD28 and CD137. First generation CARs have failed to show efficacy in the clinic—potentially due to the lack of activity and long-term persistence of the CAR-T cells in patients (Kershaw et al. 2006)—while third generation CARs have yet to show their utility in a clinical setting.

To date, the extracellular recognition domains of CARs are almost exclusively scFv's (with the few exceptions instead utilizing the extracellular domains of ligands or receptors), which is due to the fact that a single-chain functional protein (or monomer) is required to facilitate a straightforward fusion design. Accordingly, a tetrameric mAb or even a dimeric Fab would present severe challenges as an extracellular recognition domain.

Although successes have been demonstrated with various scFv approaches, that construct is an artificial fusion protein of the variable regions of the heavy (VH) and light chains (VL) of an antibody, connected with a short linker peptide of ten to about 25 amino acids. This artificial design leads to scFv-specific problems that are well known in the art. Indeed, scFv's typically display poor biophysical and developability behavior, such as low stability, bad expression yields (Haisma et al. 1998a; Haisma et al. 1998b, Peipp et al. 2004), the potential failure to be efficiently secreted in mammalian cells (Brocks et al. 1997) and, importantly, an oftentimes strong tendency to aggregate (see e.g. Ewert et al. 2003a; Ewert et al. 2003b; Schaefer et al. 2012).

When an scFv is used for the construction of a CAR, these properties can be deleterious at multiple stages. First, the generation of a well-behaved scFv is difficult, and may require extensive optimization and engineering. Second, in the scFv-containing CAR, poor biophysical behavior can lead to poor and potentially unpredictable cell surface expression, reducing the number of CARs available to bind to a target antigen. Third, the tendency of an scFv to aggregate may lead to an undesired clustering of CARs on the T-cell surface, consequently leading to an undesired spurious activation of the T-cell in the absence of any specific target-bearing cell. The latter two issues can be a serious threat to the efficacy and safety of any given CAR, presenting clear challenges to obtain a predictable and well-behaved CAR-T system.

The use of a polypeptide that employs a naturally occurring secondary and tertiary structure could provide pronounced benefits to an scFv approach. A mutein of a lipocalin that binds to a desired tumor target is an example of a suitable alternative. A lipocalin mutein, or Anticalin®, is an engineered binding protein based on a lipocalin (preferably of human origin) such as Tear Lipocalin (TLc) or NGAL. Unlike an antibody, an Anticalin is a single-domain protein; and unlike an scFv, an Anticalin is single-domain by nature, therefore per se a well-behaved monomer from a biophysical property standpoint. Apart from exhibiting superior biophysical properties, Anticalins provide tunable affinities from nanomolar to low picomolar range, while having a demonstrated ability to engage targets across a broad spectrum, including immune checkpoints.

Another application of a CAR-T involves engineering these cells with the capacity to secrete proinflammatory cytokines. In this vein, the engineered CAR-T can lead to accumulation of a proinflammatory cytokine in the tumor micronenvironment where the CAR-T traffics. A proinflammatory cytokine may be desired to facilitate recruiting a second wave of immune cells in a locally restricted fashion to initiate a more complete and potentially target-independent attack of the cells of the tumor. This approach, as recently reviewed (Chmielewski et al. 2014), has been described in particular utilizing an engineered single-chain variant of Interleukin 12, thereafter called scIL-12. Here, secretion of scIL-12 can either be constitutive or be coupled to activation of the T-cell via the CAR. The latter approach has in some instances been termed TRUCK ("T-cells redirected for universal cytokine killing"), which is why in the following the approach and related approaches are termed "TRUCK-like".

A TRUCK-like approach with constitutive scIL-12 expression has already been brought to the clinic in two separate trials, which currently are suspended (NCT01236573) or terminated (NCT01457131), respectively. Potentially, constitutive expression of scIL-12 was not sufficiently localized to lead to the desired effects, or led to intolerable toxicity.

To improve localized scIL-12 secretion, CAR-T cells have been transduced with the scIL-12 construct expressed under control of the nuclear-factor of the activated T-cell (NFAT)-derived minimal promoter to initiate IL-12 transcription upon signaling of the TCR/CD3 pathway (Chmielewski et al. 2011b; Zhang et al. 2011). Other promoters sensitive to signals of the same pathway, like the IL-2 promoter (Jaalouk et al. 2006) may also be feasible and could allow tuning the produced amount and the selectivity of cytokine production.

Using inducible scIL-12 expression, improved tumor reduction was observed compared to unmodified CAR-T cells in preclinical models (Chmielewski et al. 2011b; Zhang et al. 2011; Pegram et al. 2012; Pegram et al. 2014). Other cytokines, such as IL15, IL-18, IL-23, IL-27 and IFN-gamma, and other producer cells, such as NK cells, have been proposed for the approach. (Chmielewski et al. 2014).

The ability to engineer a T-Cell to secrete yet other types of therapeutic proteins upon T-Cell activation would be desirable, further expanding the repertoire to therapeutic modalities available in the tumor microenvironment. Particularly desirable would be specific binding proteins, e.g. a monoclonal antibody, that could bind to an immunomodulatory target, such as an immune checkpoint like CTLA4 or PD1, or to a costimulatory target such as CD137 or OX40. There are at least two drawbacks to using an antibody in this setting, however. First, antibodies are extremely large, tetrameric proteins, limiting the ability of a T-Cell to produce and secrete a functional antibody. Second, antibodies typically have a half-life in man of two to three weeks, which limits their application in an immunomodulatory approach, given potential safety concerns.

A smaller, more stable monomeric polypeptide having a shorter half-life could overcome these two shortcomings of antibodies. An example for such a molecule would be a mutein of a lipocalin that is specific for an immunomodulatory target and is monomeric, stable and has a half-life tunable from hours to days in man and a molecular weight as low as 18 kilodalton.

DETAILED DESCRIPTION

In one aspect, the disclosure provides a CAR that contains a polypeptide defining a naturally occurring monomeric motif (e.g. a lipocalin mutein) specific to a predetermined antigen (e.g., a target differentially expressed on the surface of a tumor cell) that is transduced into a T cell membrane to serve as an antigen receptor, offering benefits over conventionally deployed antibody-derived protein moieties such as a single chain variable fragment (scFv). Benefits include a more stable structure, leading to superior target engagement, for example. As used herein, a "naturally occurring motif" is hereby defined as a motif that can be found endogenously in a reference species, such as human; for example, a lipocalin is a naturally occurring motif (as is a lipocalin mutein that maintains the supersecondary or tertiary structure of a lipocalin), whereas a polypeptide such as a scFv is not a naturally occurring motif. Accordingly, "motif" when used herein in the context of a "naturally occurring motif" is preferably a naturally-occurring structure, preferably a polypeptide. Said structure preferably exists endogenously in a reference species. The skilled worker is able to readily determine whether an engineered polypeptide defines such a naturally occurring motif.

In a preferred embodiment a polypeptide defining a naturally occurring monomeric motif is not a scFv. However, that being so, a polypeptide defining a naturally occurring monomeric motif may comprise a scFv, however, in addition to a further monomeric polypeptide which is not a scFv. For example, a polypeptide defining a naturally occurring monomeric motif may comprise a scFv and a lipocalin, e.g. fused by a spacer, such as a linker amino acid sequence. Both the scFv and the further monomeric polypeptide which is not a scFV, may be specific to the same predetermined antigen or may be specific for different predetermined targets. This means that the scFv binds to a predetermined target that is different from the predetermined target to which the further monomeric polypeptide which, however, is not a scFv, binds to.

When referred to herein a "polypeptide that defines a naturally occurring motif" includes that such a polypeptide may be modified (engineered) to be able to bind to a target associated with a tumor. For example, a lipocalin, that is within the context of the present invention a polypeptide that defines a naturally occurring motif, binds to its natural target such as lysozyme in case of tear lipocalin (TLC) or iron in case of LCN2/NGAL. However, such lipocalins can be modified such that they bind to a target other than their natural target. Hence, the term "naturally occurring motif" includes, that a polypeptide defining such a naturally occurring motif that can be found endogenously in a reference species, can preferably be modified or engineered to bind to a target associated with a tumor. Yet, the modification is preferably not a modification resulting in the generation of a scFv.

The skilled worker will appreciate that the following elements are to be considered when designing a CAR:
  (i) The CAR primary sequence, consisting of a fusion of the binding element, linker region, transmembrane domain and intracellular signaling domains
  (ii) The method used to transduce a T-cell
  (iii) Suitable assays such as an in vitro assay, to test the functionality of the CAR
  (iv) In-vivo assays to test the functionality of the CAR Several designs are possible for such a CAR, with the following to be regarded as a non-limiting example. The tumor-targeting moiety of a CAR-T may comprise a mutein of a polypeptide that, endogenously, defines a monomeric polypeptide, such as a lipocalin. The target to which such mutein (e.g., an Anticalin) may bind includes CAIX, CD19, CD20, CD22, CD30, CD33, CD44v7/8, CEA, EGP-2, EGP-40, FBP, Fetal acetylcholine receptor, GD2, GD3, Her2/neu, IL-13R-a2, KDR, k-light chain, L1 cell adhesion molecule, LeY, MAGE-A1, Mesothelin, MUC1, NKG2D ligands, Oncofetal antigen (h5T4), PSCA, PSMA, TAG-72, VEGF-R2, the α-Folate receptor and others. Other tumor-associated targets that might be considered of interest in this context include EGFR, EPHA2, melanoma 30 associated chondroitin sulfate proteoglycan, IGFR1, fibroblast-activating protein alpha, c-MET, EpCAM, and GPC-3. Further, targets not directly expressed on the tumor cell surface, but associated with the tumor stroma, such as VEGF-A or Ang2, are suitable.

The linker region and transmembrane domain have the function of stably anchoring the CAR in the cell membrane, while providing for a certain distance between the membrane and the binding element to allow for an effective and activatory formation of the CAR/target complex upon an encounter of the T-cell and the target cell. Typical linker regions described in published examples lead to dimerization of the CAR. When such linker domains are used, the cytoplasmic tail of the dimeric CAR therefore contains two copies of the respective intracellular signaling regions, copying what is found in nature for the T-cell receptor (2 copies of CD3zeta) and the homodimeric receptor CD28. SEQ ID NO: 4 represents the amino acid sequence of one such example, based on a linker region and the transmembrane domain of CD8 alpha (cf. WO2014011988 A2; for all SEQ ID NO's of this application, one of the possible DNA sequences encoding the respective amino acid sequence is provided below as detailed in Table 1).

As described to date, a CAR may contain up to three intracellular signaling domains in tandem, one of which being a full intracellular signaling domain of CD3zeta (SEQ ID NO: 5) and located at the C-terminus. In second-generation CARs, an additional costimulatory signaling domain is inserted between the transmembrane domain and the CD3zeta intracellular domain; for example, the full intracellular domain of CD28 (SEQ ID NO: 6) or that of CD137 (SEQ ID NO: 7). Alternatively, the intracellular signaling domain of ICOS or of other costimulatory receptors from the TNFR family, including but not limited to Ox-40, CD27 or CD40, may also be employed. In third-generation CARs, three of these costimulatory domains can be combined, with a typical example consisting of the combination CD137, CD28 and CD3zeta. A mutein of a polypeptide that, endogenously, defines a monomeric polypeptide (such as a lipocalin) can be employed in a first, second, third or future generation CAR.

The tumor-binding moiety may, for example, be an Anticalin specific for a target selected from the group consisting of c-Met and GPC-3. The sequence of such an Anticalin binding c-Met is provided by SEQ ID NO: 1, while the sequence of an Anticalin binding GPC-3 is provided by SEQ ID NO: 2. As the linker and transmembrane region, the CD8 linker and transmembrane region (SEQ ID NO: 4) may be utilized. For intracellular signalling, the intracellular signaling domain of CD3zeta (SEQ ID NO: 5), either in tandem with CD28 (SEQ ID NO: 6) or CD137 (SEQ ID NO: 7), can be employed. The resulting four constructs, accordingly, could be: c-Met-CD28-CD3zeta (SEQ ID NO: 8), c-Met-CD137-CD3zeta (SEQ ID NO: 9), GPC3-CD28-CD3zeta (SEQ ID NO: 10) and GPC3-CD137-CD3zeta (SEQ ID NO: 11).

A number of methods have been devised to genetically modify lymphocytes ex vivo to overexpress CARs. Retroviral vectors are established and currently widely used, allowing for permanent and heritable CAR expression due to their integration into genomic DNA. For example, retroviral vectors derived from gamma-retrovirus have been utilized for lymphocyte gene transfer in clinical applications since 1990 (Rosenberg et al. 1990). As an alternative, an HIV-based lentiviral vector may provide advantages such as higher and more stable expression of the transgene, and potentially increased safety compared to gamma-retroviral vectors. Other possible methods for gene transfer include electroporation of mRNA constructs, if CAR expression is desired to be transient only (Birkholz et al. 2009); (Zhao et al. 2006), and transposon-based systems such as "piggybac" and "sleeping beauty" (Maiti et al. 2013). A retrovirus-based system based on the vector pBULLET, as described in Willemsen et al. 2000, is utilized in this application to express SEQ ID NOs: 8-11. Alternatively, pSTITCH (Weijtens et al. 1998) also may be employed.

One or more in vitro assays can be employed to test the functionality of a CAR, using standard methods that serve to demonstrate the activation of T-cells. Investigations include the responses of T-cells to activation, namely proliferation and prolonged survival, the production of cytokines such as IL-2 and IFN-gamma, and the capacity to kill target cells. The latter can be determined, e.g., by direct observation of target cell killing, but also by indirect methods that show for example the release of intracellular components of the target cell or the generation of cytotoxic molecules by the T-cells.

To investigate the functionality of a given CAR-design in vivo, mouse models may be employed.

Examples for both in-vitro and in-vivo assays are provided in the literature, cf. for example Hombach et al. 2010; Chmielewski et al. 2011a; Chmielewski et al. 2011b; Kofler et al. 2011; Chmielewski et al. 2012; Maliar et al. 2012; Pegram et al. 2012; Chmielewski et al. 2013a; Chmielewski et al. 2013b; Hombach et al. 2013; Pegram et al. 2014; and Textor et al. 2014.

The skilled worker also will appreciate that beyond a lipocalin mutein, other monomeric or single domain polypeptides can be employed, including but not limited to a DARPin, a Fynomer, and a Kunitz domain peptide.

In another aspect, the disclosure provides a CAR that secretes a polypeptide, which may or may not define a naturally occurring monomeric motif (e.g. a lipocalin mutein) specific to a predetermined antigen (e.g. an immunomodulatory target such as an immune checkpoint or costimulatory molecule) that is transduced into a T cell for secretion thereby, bringing an added therapeutic benefit. In this vein, the secreted polypeptide preferably is monomeric; further, the secreted polypeptide preferably is specific for an immunomodulatory target.

This construct can be based on T-cells with a defined specificity (either without genetic manipulation or by transduction with a CAR or a recombinant TCR) that are equipped with the capacity to secrete therapeutically relevant biologics. In contrast to TRUCK-like approaches, which are based on the secretion of proinflammatory cytokines, the present disclosure provides for a T cell that secretes a specific binding polypeptide that can be antagonistic or agonistic vis-à-vis its target. In the context of oncology indications, tumor-specific T cells that secrete biologics that are antagonistic inhibitors of the interaction of co-inhibitory immune receptors with their ligands (also known as "checkpoint inhibitors") may be employed. Specific, non-limiting target examples include PD-1 and CTLA-4. Alternatively, constructs that allow the agonistic activation of stimulatory and/or costimulatory immune receptors can be utilized, with examples for the respective targets being CD3 and CD137. Further, antagonists to anti-inflammatory cytokines such as IL-10 or TGF-also can be employed. This approach can be termed T-cell activation-induced localized secretion (TAILS).

The skilled worker will appreciate that this approach can also be based on other cell types, such as NK cells or B-cells. Further, an analogous approach can be applied to auto-inflammatory conditions; however, in this case antagonists to stimulatory receptors or proinflammatory cytokines or agonists of coinhibitory immune receptors may be applied, and vehicle cells that have no cytotoxic capacity may be employed.

TAILS can be viewed as an extension of the CAR-T/Recombinant TCR approaches with an improved efficiency. On the other hand, TAILS can also be viewed as an alternative to traditional biologics, where production of the therapeutic occurs in vivo. This firstly provides the advantage of highly localized (ant-)agonism with concomitant minimal unwanted systemic toxicity, in particular if biologics with a low systemic half-life are employed, and secondly facilitates efficient delivery of biologics to any site of action within the human body, including tissues which would otherwise not be reachable by biologics drugs that are systemically applied, such as the brain. Furthermore, local delivery of biologic therapeutics has the potential to not only have a more benign toxicity profile, but also to display an improved efficacy as it is well known that local and systemic effects of agonists or antagonists can be profoundly different.

The skilled worker will appreciate that the following elements are to be considered when designing the components of a TAILS system according to the foregoing principles:

(i) The biologic used as a secreted antagonist or agonist
(ii) The target of the CAR or (recombinant) TCR
(iii) The target of the secreted biologic
(iv) The cells used as vehicles and producers of the single-chain biologic
(v) The method used to transduce the vehicle cells
(vi) In-vitro and in-vivo assays to test the functionality of the TAILS system Several designs are possible for the biologic used as a secreted (ant-)agonist, with the following to be regarded as a non-limiting example. In theory, both TRUCK-like or TAILS approaches can be implemented using proteins consisting of multiple subunits (i.e. multiple polypeptide chains); for example, a heterodimeric cytokine such as IL-12 consisting of the IL-12p40 and the IL-12p35 subunits, or an IgG antibody consisting of two heavy chains and two light chains, as such multimeric proteins might be assembled within a vehicle cell that is transduced with all the subunits endcoded on suitable vectors. However, a complex multimeric protein may incorrectly inefficiently assemble, leading either to secretion of an undesired product with concomitant undesired effects (for example an IL-12p40 dimer), or insufficient generation and secretion of the multimer (for example an antibody). Therefore, biologics used for TAILS should preferably define a monomer, with examples including but not limited to Affibody molecules, Affilins, Affimers, Affitins, Anticalins, Avimers, DARPins, Fynomers, Kunitz domain peptides, Monobodies or single-chain variants of Antibodies such as scFv and their derivatives, camelid single-chain Antibodies, nanobodies or domain Antibodies.

The targets recognized by the T-cell, either by the physiological (T-cell) receptor, a CAR or recombinant TCR, include, but are not limited to the targets described above. Here, it is of note that targets that are tumor-associated but not necessarily tumor cell-associated (such as VEGF-A, Ang2 and others) may be particularly suited to provide local release of a checkpoint inhibitor or an immune receptor agonist without inducing cell killing of specific cells. If a CAR is employed in the approach, the overall design will follow the principles described herein for the Anticalin-based CAR.

Potential targets of the secreted biologic include coinhibitory receptors or their ligands such as CTLA-4, B7-1, PD-1, PD-L1, LAG3, BTLA, TIM3, TIGIT, CD160 or LAIR1. (Chen et al. 2013) Here, the secreted biologic must be capable of interfering with the ligand/receptor interaction or must otherwise block downstream signaling. Alternatively, constructs that allow the agonistic activation of stimulatory and/or costimulatory immune receptors can be utilized, with examples for receptors being the TCR (e.g. via CD3), CD28, ICOS, CD137, Ox40, GITR, HVEM, CD27, CD30, DR3, SLAM, CD2 or CD226. (Chen et al. 2013) Depending on the target, such agonists can for example be obtained by dimerisation or multimerisation of a single receptor binder.

For this purpose, mobile cells that have the capacity to strongly proliferate upon activation, and that are capable of secreting sufficient amounts of a given biologic are required. T-, B- and NK cells, and, where applicable, their subtypes are in principle amenable to this task. How this would be done in practice is well known in the art for T-cells (cf. CAR-T approach), and could analogously be implemented for the other cell types.

Methods for cell transduction of a CAR or TCR can be followed as described herein. Vectors suitable for T-cell activation driven secretion are described in the literature, cf. e.g. Chmielewski et al. 2011b; Zhang et al. 2011; Pegram et al. 2012 and Pegram et al. 2014.

The assays used to characterize engineered lymphocytes capable of TAILS can be essentially the same as the ones described for CAR- or TCR-transduced T-cells above. Additionally, assays can be used to measure successful secretion of the therapeutic produced by the cells, with ELISA assays being a straightforward possibility.

A representative example, below, is based on a CAR-T cell generated by transduction of T-cells with the construct GPC3-CD137-CD3zeta (SEQ ID NO: 11) described herein. The T-cell may be co-transduced with a suitable vector encoding the secreted biologic; for this purpose, an Anticalin-based CTLA-4 antagonist (SEQ ID NO: 3), which binds both human and mouse CTLA-4, can be employed.

Also provided by the present invention is a pharmaceutical composition comprising a T cell as described herein and optionally a pharmaceutically acceptable carrier.

Furthermore, the present invention provides a T cell as described herein for use in a method of treatment of cancer.

Similarly, the present invention provides a method of treatment of cancer comprising administering to a subject in need thereof a pharmaceutically efficient amount or numbers of T cells as described herein.

The treatment of cancer includes the treatment of a tumor. The subject is preferably a mammal, more preferably a human. A pharmaceutically acceptable carrier also includes a pharmaceutically acceptable excipient.

FIGURES

FIG. 1: Inducible expression of CTLA-4 antagonist in primary T cells analyzed by FACS. Human peripheral blood T cells were transduced with pSIN-(NFAT)6-αCTLA-4 and incubated for 48 h at 37° C. under activatory conditions by utilizing plates precoated with anti-CD3 mAb and anti-CD28 mAb. Cells were stained extracellularly using a FITC-labeled anti-CD3 antibody, and intracellularly—after fixation and permeabilization—for SEQ ID NO: 28 utilizing a primary polyclonal anti-NGAL rabbit antibody, followed by secondary staining with a Dylight594-conjugated anti-rabbit IgG antibody. Immunofluorescence was analyzed using a FACS instrument. A detailed protocol of the experiment is provided in Example 1.

Figure 2:
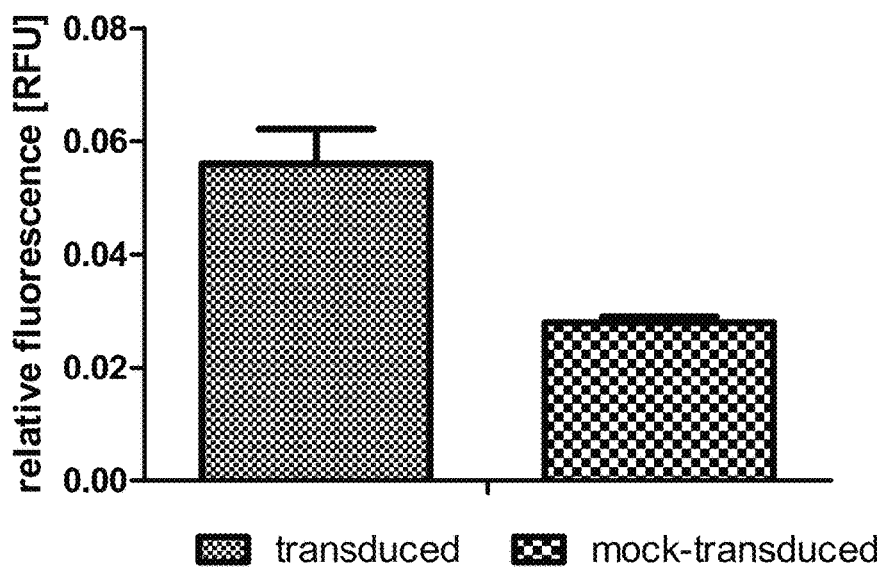

FIG. 2: Detection of functional T-cell secreted CTLA-4 antagonist by ELISA. The supernatant of human peripheral blood T cells, mock-transduced or transduced with pSIN-(NFAT)6-αCTLA-4 and cultured under activatory conditions (cf. Example 1 and FIG. 1) was analyzed for the presence of functionally active CTLA-4 antagonist SEQ ID NO: 28 by ELISA. Recombinant human CTLA-4 was coated on an ELISA plate as described in Example 1, and culture supernatants of transduced and mock-transduced T cells were added. Plate-bound SEQ ID NO: 28 was detected by primary staining with an anti-NGAL polyclonal antibody from the rabbit, secondary staining using goat anti rabbit IgG-HRP and addition of a chromogenic HRP substrate as described in Example 1.

Figure 3:
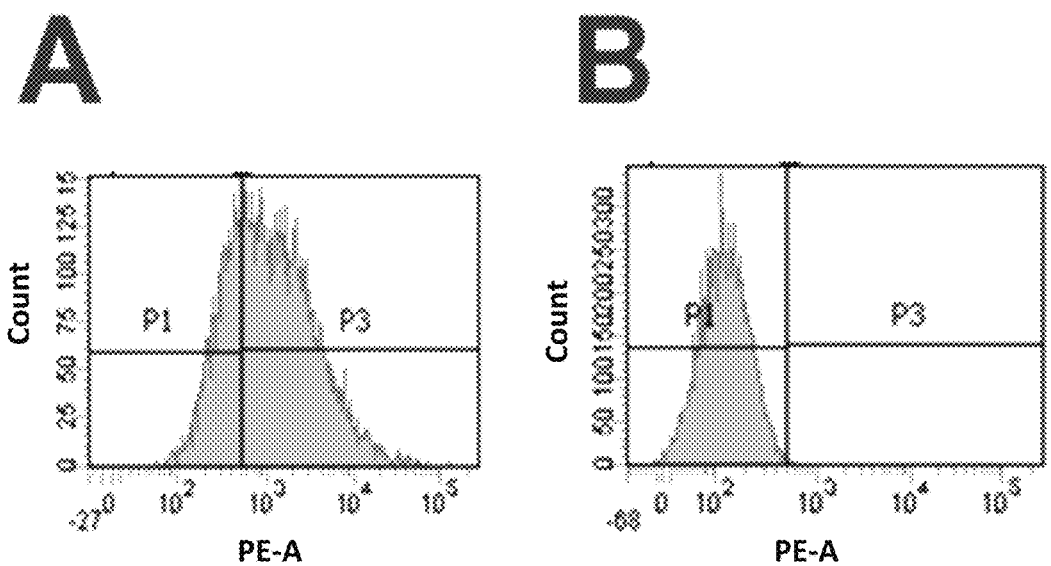

FIG. 3: Detection of functional T-cell secreted CTLA-4 antagonist by FACS of CTLA-4-positive CHO cells. The supernatant of Jurkat cells transduced with pSIN-(NFAT)6-αCTLA-4 and cultured under activatory conditions (cf. Example 2) was analyzed for the presence of functionally active CTLA-4 antagonist SEQ ID NO: 28 by incubation of the supernatant with CHO cells stably expressing CTLA-4 on their surface (CHO::CTLA-4). As a control, CHO::CTLA-4 were incubated with isotype control. Cell-bound SEQ ID NO: 28 that had been excreted by the Jurkat cells was then detected using anti-NGAL polyclonal antibody followed by secondary staining with a fluorescently labeled anti-rabbit Antibody as described in Example 2.

Figure 4:
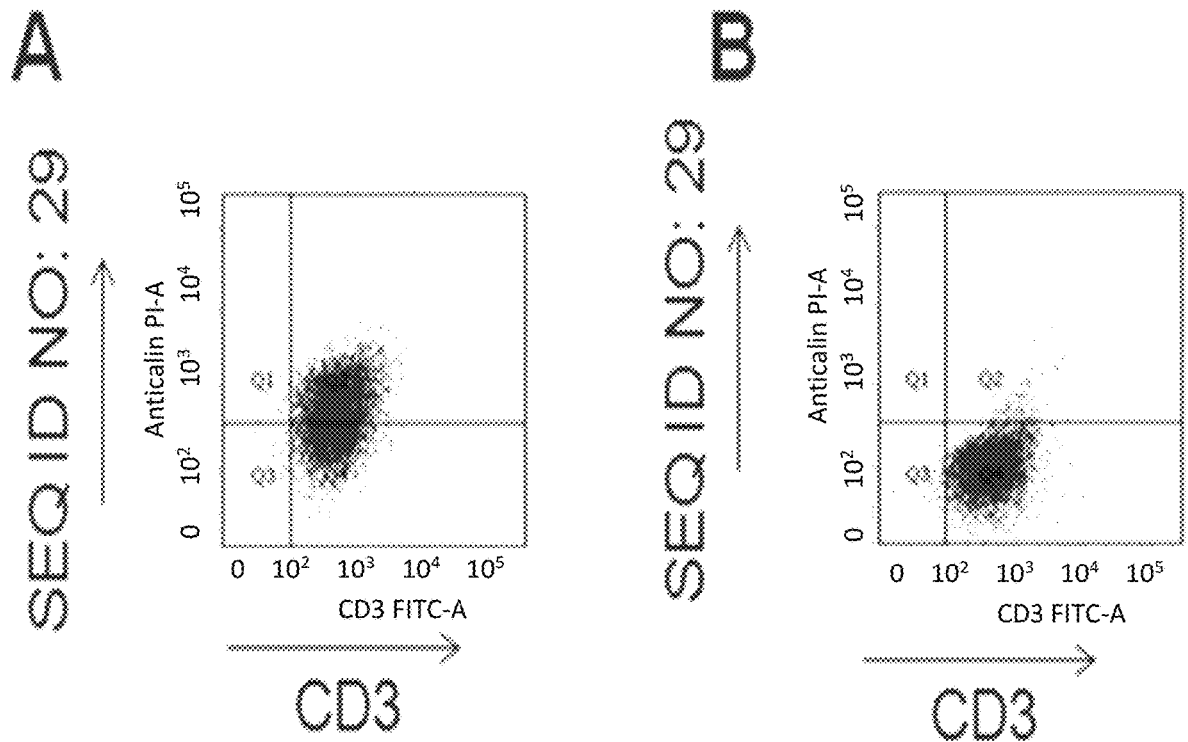

FIG. 4: Inducible expression of Fc fusion of CTLA-4 antagonist in primary T cells analyzed by FACS. Human peripheral blood T cells were transduced with pSIN-(NFAT)6-αCTLA-4-Fc and incubated for 48 h at 37° C. under activatory conditions by utilizing plates precoated with anti-CD3 mAb and anti-CD28 mAb. Cells were stained extracellularly using a FITC-labeled anti-CD3 antibody, and intracellulary—after fixation and permeabilization—for SEQ ID NO: 29 utilizing a primary polyclonal anti-NGAL antibody, followed by secondary staining with a Dylight594-conjugated anti-rabbit IgG antibody. Immunofluorescence was analyzed using a FACS instrument. Cf. Example 3 for details.

Figure 5:
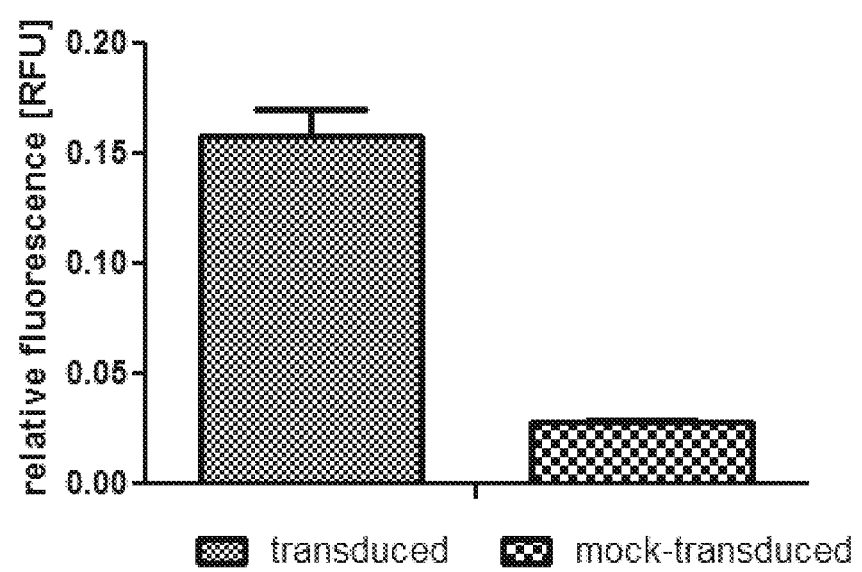

FIG. 5: Detection of functional T-cell secreted Fc fusion of a CTLA-4 antagonist by ELISA. The supernatant of human peripheral blood T cells, mock-transduced or transduced with pSIN-(NFAT)6-αCTLA-4-Fc and cultured under activatory conditions (cf. Example 3 and FIG. 4) was analyzed for the presence of the functionally active Fc fusion of the CTLA-4 antagonist SEQ ID NO: 29 by ELISA. Recombinant human CTLA-4 was coated on an ELISA Plate as described in Example 3, and culture supernatants of transduced and mock-transduced T cells were added. Plate-bound SEQ ID NO: 29 was detected by primary staining with an anti-NGAL polyclonal rabbit antibody, secondary staining using goat anti rabbit IgG-HRP and addition of a chromogenic HRP substrate as described in Example 3.

WORKING EXAMPLES

A. CAR-Transduced T Cell Containing an Anticalin as CAR Moiety

Generation of CAR-Transduced T-Cells

As a first step, the coding DNA corresponding to the SEQ ID NOs: 8-11 is generated by gene synthesis. For that purpose, a set of codons that is compatible with mammalian expression needs to be employed. The DNA stretches encoding the CARs are equipped with suitable restriction sites at the N- and C-termini to allow cloning into the retroviral expression vector pBullet (Willemsen et al. 2000), or, alternatively, pSTITCH (Weijtens et al. 1998). The gene synthesis is straightforwardly performed using a commercial provider, and the resulting DNA is cloned into pBullet using standard molecular biology methods.

To obtain retroviral particles suitable for peripheral blood T-cell transduction we proceed as described (Weijtens et al. 1998). In short, DNA of the respective retroviral vector (pBullet or pSTITCH) containing the Anticalin-based CAR (6 mg DNA) is co-transfected into 293T cells by calcium phosphate co-precipitation with the retroviral helper plasmid DNA pHIT60 and pCOLT (each 6 mg DNA) encoding the MuLV gag and pol genes (pHIT60) and the GALV envelope gene (pCOLT), respectively, under control of the CMV promotor/enhancer (Weijtens et al. 1998). This procedure results in transient production of high titers of infectious retrovirus. Peripheral blood lymphocytes from healthy donors are isolated by density centrifugation and cultured for 48 h in RPMI-1640 medium supplemented with 10% FCS in the presence of IL-2 (400 U/ml) and OKT3 MAb (100 ng/ml). Cells are harvested, washed, resuspended in medium with IL-2 (400 U/ml), and co-cultured for 48 h with 293T cells that are transiently transfected as described above and therefore produce and excrete the retroviral transducing particles into the medium. In the final step, T cells are harvested and subsequently tested for successful CAR expression and functional assays as described further below.

Characterisation of CAR-Transduced T-Cells—FACS

Successful cell-surface expression of the chimeric antigen receptor on transduced T-cells is demonstrated by multicolor immunofluorescence, using the fluorescence-labeled, soluble extracellular domains of the respective targets human c-Met and human GPC-3, or alternatively, an anti-CD8 antibody detected by a suitable fluorescence-labeled secondary antibody. Immunofluorescence is analyzed using a suitable FACS instrument. Transduced cells labeled in this manner show a clear fluorescence signal in FACS compared to a non-transduced T-cell control.

Characterisation of CAR-Transduced T-Cells—T-Cell Activation on Coated Plates

To investigate whether signaling via the CAR leads to T-cell activation, we can conduct two experiments with coated protein to cluster the CAR on the transduced T-cells. This is either accomplished by plastic-coating an anti-CD8 antibody on a microtiter plate or by coating the target protein of the CAR (either c-Met or GPC-3 depending on the construct). A non-binding IgG1 Antibody serves as the negative control. The microtiter plates are coated with 1-50 μg/ml of the anti-CD8 antibody, c-Met, GPC-3 or control IgG1. Transduced and non-transduced peripheral blood T cells (1-3 $10^5$ cells/well) are incubated for 48 h at 37° C. in the coated microtiter plates. After 48 h, culture supernatants are analyzed for IFN-g by ELISA using a suitable commercial kit.

The supernatant of CAR-expressing T-cells incubated in plastic well coated with either an anti-CD8-antibody or with the targets c-Met or GPC3, respectively, contains significantly more IFN-gamma than that of the controls. The latter are either T-cells not expressing a CAR, or CAR-transduced T-cells incubated in wells coated with the control IgG1.

Characterisation of CAR-Transduced T-Cells—T-Cell Activation by Coculture with Target-Expressing Mammalian Cells In a second step, which is more akin to the desired situation in-vivo, different amounts of receptor-grafted T cells (1.25 to $10 \times 10^4$ cells/well) are co-cultured for 48 h with GPC-3+ or c-Met+ immortal tumor cell lines. Target-positive cell lines that can be used are HepG2 (GPC-3) and H441 (c-Met), and examples for GPC-3/c-Met-negative control cells are SK-HEP-1 (GPC-3) and A2870 (c-Met). As a further control for T-cell CAR specificity, we co-incubate non-transduced T-cells with GPC-3+ or c-Met+ cells. In all cases, cells are coincubated for 48 h, and supernatants are subsequently analysed for IFN-gamma expression.

We find that the supernatant of CAR-transduced T-cells cocultured with the target-matched immortal cell lines contains significantly more IFN-gamma than the controls, clearly showing CAR-specific T-cell activation.

Characterisation of CAR-Transduced T-Cells—Measurement of Cytotoxicity of T-Cells Cocultured with Target-Expressing Mammalian Cells Specific cytotoxicity of receptor-grafted T cells to target cells is measured by lactate dehydrogenase (LDH) release. Briefly, receptor-grafted and non-transduced T cells (L25-

$10 \times 10^4$ cells/well) are co-cultured for 12 hr with $1-3 \times 10^4$ cells/well of either GPC3+, c-Met+, GPC3− or c-Met-cells, respectively, in round-bottomed microtiter plates. Effector-to-target ratios range from 10 to 1. To determine spontaneous, baseline LDH release, T cells are cultured without target cells. LDH in culture supernatants (100 ml/well) is determined utilizing a suitable commercial kit. The percentage of specific cytotoxicity is calculated by correcting for spontaneous release and normalizing to the maximum LDH release determined after addition of 1% (v/v) Nonidet P-40.

We find that the specific cytotoxicity of the Anticalin-CAR based T-cells is significantly higher in the presence of the matched, target-positive tumor cell lines than in the presence of the target-negative tumor cell lines. Additionally, non-transduced T-cell preparations show a much reduced specific cytotoxicity compared to the transduced T-cells.

In-Vivo Characterization of CAR-Transduced T-Cells

The following experiment is performed in analogous fashion to Chmielewski et al. 2011b. In brief, human T cells are isolated from peripheral blood by magnetic activated cell sorting, using human CD3+ beads. The transduction-competent retroviri encoding the c-Met- and GPC3-specific CARs are generated and used for transduction of human T-cells as described above. For the mouse studies, we use the NIH-III mouse (Charles River), which is deficient in NK cells, B cells, and T cells. MC38 cells stably transfected with human GPC-3 or c-Met ($9 \times 10^5$ cells/mouse) are s.c. coinjected together with the engineered, specificity matched T cells ($2 \times 10^5$ T cells/mouse) into NIH-Ill mice (6-7 mice per group). Alternatively, tumors are induced by s.c. injection of MC38 cells stably transfected with human GPC-3 or c-Met and matched CAR-T cells are applied by i.v. injection at day 6. The respective experiment using CAR-T cells and the mismatched transfected tumor cell line serves as a negative control. Tumor growth is monitored daily by external measurement with a digital caliper.

In the experiments, we find a significant delay in tumor outgrowth when target-positive cells and target-specific CAR-T cells are injected into the same mouse compared to negative controls.

B. CAR-Transduced T Cell Containing an Anticalin as TAILS Moiety

Generation of CAR-Transduced T-Cells Capable of TAILS (CAR/TAILS-T)

The construct GPC3-CD137-CD3zeta (SEQ ID NO: 11) is generated and cloned into a suitable retroviral vector as described above. Retroviral particles suitable for peripheral blood T-cell transduction are obtained by co-transfection with retroviral helper particles into 293T cells, also as described above.

A vector suitable to facilitate retroviral expression of the T-cell activation inducible Anticalin-based CTLA4-antagonist ("αCTLA-4") is obtained by exchanging the mature IL-12 sequence in pSIN-(NFAT)6-IL-12 (Chmielewski et al. 2011b) by the Anticalin sequence (SEQ ID NO: 3) using standard molecular biology methods, to obtain pSIN-(NFAT)6-αCTLA-4. Note that the leader sequence of IL-12 remains in the construct to serve as a secretion signal.

In a 2-step transduction procedure, T cells are retrovirally transduced with the αCTLA-4 expression cassette and positively selected in the presence of 0.5 mg/mL Geneticin (G418) and IL-2 (500 IU/mL) on plates precoated with anti-CD3 mAb OKT-3 and anti-CD28 mAb 15E8 as previously described (Chmielewski et al. 2011b). Geneticin-resistant clones are transduced with the GPC-3-specific CAR GPC3-CD137-CD3zeta.

Characterization of CAR/TAILS T-Cells

Successful cell-surface expression of the chimeric antigen receptor on the doubly transduced CAR/TAILS T-cells is performed as described above: we employ multicolor immunofluorescence, using the fluorescence-labeled, soluble extracellular domain of human GPC-3, or alternatively, an anti-CD8 antibody detected by a suitable fluorescence-labeled secondary antibody. Immunofluorescence is analyzed using a suitable FACS instrument. Transduced cells labeled in this manner show a clear fluorescence signal in FACS compared to a non-transduced T-cell control.

Characterisation of CAR/TAILS-T-Cells—T-Cell Activation on Coated Plates and CTLA-4 Secretion To investigate whether signaling via the CAR leads to T-cell activation in the CAR/TAILS T-cell, we conduct two experiments with coated protein to cluster the CAR on the transduced T-cells, in analogy to the experiment described above. This is either accomplished by plastic-coating an anti-CD8 antibody on a microtiter plate, or, alternatively, by coating GPC-3. A non-binding IgG1 Antibody serves as the negative control. The microtiter plates are coated with 1-50 µg/ml of the anti-CD8 antibody, GPC-3 or control IgG1. Transduced and non-transduced peripheral blood T cells ($1-3 \; 10^5$ cells/well) are incubated for 48 h at 37° C. in the coated microtiter plates. After 48 h, culture supernatants are analyzed for IFN-gamma by ELISA using a suitable commercial kit. Further, supernatants are analyzed for the presence of the Anticalin-based CTLA-4 antagonist by a suitable ELISA setup.

The supernatant of CAR-expressing T-cells incubated in plastic well coated with either an anti-CD8-antibody or with GPC3, respectively, contains significantly more IFN-gamma and Anticalin-based CTLA-4 antagonist than that of the controls. The latter are either T-cells not expressing a CAR, but transduced with αCTLA-4 only (SEQ ID NO: 3), or doubly transduced CAR/TAILS T-cells incubated in wells coated with the control IgG1.

Characterization of CAR/TAILS-T-Cells—T-Cell Activation by Coculture with Target-Expressing Mammalian Cells In a second step, which is more akin to the desired situation in-vivo, different amounts of receptor-grafted T cells (1.25 to $10 \times 10^4$ cells/well) are co-cultured for 48 h with GPC-3+ immortal tumor cell lines. The GPC3-positive cell line used is HepG2, and the GPC-3-negative control cell line is SK-HEP-1. As a further control for T-cell CAR specificity, we co-incubate with GPC-3+ cells with T-cells not expressing a CAR, but transduced with αCTLA-4 (SEQ ID NO: 3) only. In all cases, cells are coincubated for 48 h, and supernatants are subsequently analysed for IFN-γ expression and the expression of the anti-CTLA-4 Anticalin.

We find that the supernatant of CAR-transduced T-cells co-cultured with the target-matched immortal cell lines contains significantly more IFN-γ and anti-CTLA-4 Anticalin than the controls, clearly showing CAR-specific T-cell activation and T-cell activation induced secretion of the CTLA-4 antagonist.

Characterisation of CAR/TAILS-T-Cells—Measurement of Cytotoxicity of T-Cells Cocultured with Target-Expressing Mammalian Cells Specific cytotoxicity of receptor-grafted T cells to target cells is measured by lactate dehydrogenase (LDH) release as described above. Briefly, doubly transduced CAR/TAILS T-cells, CAR-transduced-cells or non-transduced T cells ($1.25-10 \times 10^4$ cells/well) are co-cultured for 12 hr with $1-3 \times 10^4$ cells/well of either GPC3+, or GPC3− cells, respectively, in round-bottomed microtiter plates. Effector-to-target ratios range from 10 to 1. To determine spontaneous, baseline LDH release, T cells are cultured without target cells. LDH in culture supernatants (100 ml/well) is determined utilizing a suitable commercial kit. The percentage of specific cytotoxicity is calculated by correcting for spontaneous release and normalizing to the maximum LDH release determined after addition of 1% (v/v) Nonidet P-40.

We find that the specific cytotoxicity of the doubly transduced CAR/TAILS T-cells is at least retained compared to the CAR-only based T-cells, and significantly higher in the presence of the matched, target-positive tumor cell lines than in the presence of the target-negative tumor cell lines. Additionally, non-transduced T-cell preparations show a much reduced specific cytotoxicity compared to the transduced T-cells.

Characterisation of CAR/TAILS-T-Cells—In-Vivo Experiment

The following experiment is performed in analogy to Chmielewski et al. 2011b and above, but utilizing a different tumor cell line. In brief, human T cells are isolated from peripheral blood by magnetic activated cell sorting, using human CD3+ beads. The GPC-3-specific and αCTLA-4-Anticalin secreting CAR/TAILS-T cells are generated as described herein. For the mouse studies, we use the NIH-III mouse (Charles River), which is deficient in NK cells, B cells, and T cells. AT3 cells stably transfected with human GPC-3 ($9 \times 10^5$ cells/mouse) are s.c. coinjected together with the engineered CAR/TAILS-T cells ($2 \times 10^5$ T cells/mouse) into NIH-III mice (6-7 mice per group). Alternatively, tumors are induced by s.c. injection of AT3 cells stably transfected with human GPC-3 and CAR/TAILS-T cells are applied by i.v. injection at day 6. Negative controls include a vehicle injection control, the respective experiment using CAR/TAILS-T and mock-transfected AT3 cells, and the respective experiment utilizing CAR-T cells that do not secrete α-CTLA-4 Anticalin. Tumor growth is monitored daily by external measurement with a digital caliper.

In the experiments, we find a significant delay in tumor outgrowth when target-positive cells and target-specific CAR/TAILS-T cells are injected into the same mouse compared to the controls.

Example 1

Generation of Primary T Cells Capable of TAILS and Characterisation

A vector suitable to facilitate retroviral expression of the T-cell activation inducible Anticalin-based CTLA4-antagonist ("αCTLA-4") was obtained by replacing the IL-12 sequence in pSIN-(NFAT)6-IL-12 (Chmielewski et al. 2011b) by the Anticalin sequence (SEQ ID NO: 3) with a Strep-tag II (SEQ ID NO: 27) using standard molecular biology methods, to obtain pSIN-(NFAT)6-αCTLA-4. The leader sequence of the mouse immunoglobulin kappa light chain (GenBank Acc #CAB46127.1) instead of the IL-12 leader was employed in the construct to serve as a secretion signal. The final amino acid sequence corresponds to SEQ ID NO: 23, encoded by the DNA sequence SEQ ID NO: 24.

To obtain retroviral particles suitable for peripheral blood T-cell transduction we proceeded as described (Weijtens et al. 1998; Cheadle et al., 2012). In short, DNA of pSIN-(NFAT)6-αCTLA-4 (6 mg DNA) was co-transfected into 293T cells by calcium phosphate co-precipitation with the retroviral helper plasmid DNA pHIT60 and pCOLT (each 6 mg DNA) encoding the MuLV gag and pol genes (pHIT60) and the GALV envelope gene (pCOLT), respectively, under control of the CMV promotor/enhancer (Weijtens et al. 1998). This procedure resulted in the production of high titers of infectious retrovirus.

In order to obtain T cells transduced with pSIN-(NFAT)6-αCTLA-4, peripheral blood lymphocytes from healthy donors were isolated by density centrifugation in a Ficoll-Paque (GE Healthcare) density gradient and cultured for 48 h in RPMI1640 medium supplemented with 10% (v/v) FCS in the presence of IL-2 (400 U/ml) and OKT3 mAb (100 ng/ml). Cells were harvested, washed, resuspended in medium with IL-2 (400 U/ml), and co-cultured for 48 h with 293T cells that were transiently transfected as described above and therefore released the retrovirus particles into the medium. In the final step, T cells were harvested. The same procedure was also carried out using mock-transduction, i.e. transducing the gag, pol and env genes of the retrovirus without the expression cassette.

To investigate whether activation of the transduced T cells induced the secretion of SEQ ID NO: 28 (the mature processed form of SEQ ID NO:24), $5 \times 10^6$ cells peripheral blood T cells in 10 mL medium—transduced or mock-transduced—were incubated for 48 h at 37° C. on Nunc™ OmniTray™ plates precoated with anti-CD3 mAb OKT-3 and anti-CD28 mAb 15E8 as previously described (Chmielewski et al. 2011b). To determine both successful expression of the anti-CTLA-4 Anticalin (SEQ ID NO: 28) on the transduced TAILS T-cells and the fraction of cells that was successfully transduced, we employed multicolor immunofluorescence using a FITC-labeled anti-CD3 antibody (anti-human CD3, clone OKT3 (ATCC)), and a polyclonal anti-NGAL rabbit antibody, followed by secondary staining with an anti-rabbit antibody labeled with the fluorescent dye Dylight594. The detailed protocol was as follows, performing all incubation steps protected from light: Transduced T cells were stained for CD3 using the FITC-labeled anti-CD3 antibody for 30 minutes at 4° C., followed by fixation and permeabilization by resuspending in 250 μl BD Cytofix/Cytoperm solution and incubating for 20 minutes at 4° C., followed by washing twice in a buffer containing the cell permeabilizing agent saponin (BD Perm/Wash™ buffer, Cat. 554723). Intracellular staining of SEQ ID NO: 28 was then achieved by thoroughly resuspending the fixed and permeabilized cells in 50 μL of a saponin-containing buffer (BD Perm/Wash™ buffer) containing 0.5 μg anti-NGAL mAb per 1 million cells, washing twice with saponin-containing BD Perm/Wash™ buffer, and incubation for 30 minutes at 4° C. with 1 μg of the Dylight594-conjugated anti-rabbit IgG antibody per 1 million cells. Finally, cells were washed twice with PBS buffer and immunofluorescence was analyzed using a BD FACS Canto II instrument. In the FACS analysis, transduced cells labeled in this manner showed a clearly positive anti-NGAL reactivity (FIG. 1A) compared to the mock-transduced T-cell control (FIG. 1B). We found that according to a threshold set based on the mock-transduced T-cell control (FIG. 1B), 52% of primary T cells had been transduced and were found to be SEQ ID NO: 28-positive.

Supernatants were analyzed for the presence of functionally active Anticalin-based CTLA-4 antagonist by ELISA as described in the following: Recombinant human CTLA-4 at a concentration of 5 μg/mL in PBS was added to each well of a 384 well ELISA plate and incubated over night at 4° C. All following steps were performed with 1 h incubation time and repeated washing with PBS/0.05% (w/v) Tween20 (PBS-T). In the first step, plates were blocked (BSA 2% (w/v) in PBS-T/0.1% (w/v) Tween 20) and 20 μL of culture supernatants were added. Subsequently, rabbit anti-NGAL polyclonal antibody at a concentration of 1 µg/mL in PBS/ 0.1% (w/v) Tween20/2% (w/v) BSA was added, and bound antibody was detected using goat anti-rabbit IgG-HRP in a dilution of 1:5,000 in PBS/0.1% (w/v) Tween20/2% (w/v) BSA. Chromogenic 3,3',5,5;-tetramethylbenzidine (TMB) substrate was used as a detection agent according to the manufacturer's instructions (Life Technologies). Fluorescence signals in RFU (relative fluorescence units) were measured using a plate fluorescence reader.

We found a clear anti-CTLA-4 reactivity in supernatants of pSIN-(NFAT)6-αCTLA-4-transduced and activated T cells compared to the supernatants of mock-transfected cells (FIG. 2). Note that the mock-transfected cells showed a background fluorescence signal due to nonspecific matrix effects, which was, however, significantly below the positive ELISA signal of the supernatant of pSIN-(NFAT)6-αCTLA-4-transduced cells.

Example 2

Target Cell Binding of TAILS-Produced Anti-CTLA-4 Anticalin

The experiment of this example was carried out in analogy to Example 1, but using the Jurkat T cell line instead of primary T cells. In short, Jurkat T cells were transduced with pSIN-(NFAT)6-αCTLA-4 as described in Example 1, and incubated in medium on plates precoated with anti-CD3 mAb OKT-3 and anti-CD28 mAb 15E8 as previously described (Chmielewski et al. 2011b).

The culture supernatant containing the anti-CTLA-4 Anticalin (SEQ ID NO: 28) was obtained from the Jurkat cells by centrifugation and added to Chinese Hamster Ovary cells stably transfected with CTLA-4 (CHO::CTLA-4). As a control, CHO::CTLA-4 were incubated with an isotype control antibody. Cell-bound SEQ ID NO: 28 was detected using anti-NGAL rabbit polyclonal antibody followed by staining with anti-rabbit antibody labeled with the fluorescent dye Dylight594. In the FACS fluorescence histogram (FIG. 3), a clear shift in fluorescence intensity for cells incubated with the supernatant from pSIN-(NFAT)6-αCTLA-4-transduced Jurkat cells compared to the isotype control is evident, showing the binding of excreted SEQ ID NO: 28 to CTLA-4 positive cells.

Example 3

Generation of Primary T Cells Capable of Inducible Secretion of an Fc-Fusion of Anticalin-Based CTLA-4 Antagonist and Characterisation The experiments described here were performed in full analogy to Example 1, but utilizing SEQ ID NO: 25, which is a fusion of the Anticalin-based CTLA-4 Antagonist (SEQ ID NO: 23) to the Fc fragment of a human IgG1 antibody. The DNA sequence encoding SEQ ID NO: 25 is provided by SEQ ID NO: 26. The corresponding inducible expression vector pSIN-(NFAT)6-αCTLA-4-Fc was generated by standard molecular biology methods.

Generation of retroviral particles suitable for peripheral blood T-cell transduction, as well as T cell preparation and transduction with pSIN-(NFAT)6-αCTLA-4-Fc, were performed as described in Example 1. Mock-transduction was used as a control. To investigate whether activation of the transduced T cells lead to secretion of SEQ ID NO: 29 (the mature processed form of SEQ ID NO:25), we proceeded with multicolor FACS staining of the targets CD3 and SEQ ID NO: 29 as described in Example 1. In the FACS analysis, transduced and fluorescence-labeled cells showed a clearly positive anti-NGAL reactivity (FIG. 4A) compared to the mock-transduced T-cell control (FIG. 4B). We found that according to a threshold set based on the mock-transduced T-cell control (FIG. 4B), 63% of primary T cells had been transduced and were found to be SEQ ID NO: 29-positive.

Supernatants were analyzed for the presence of functionally active Anticalin-based CTLA-4 antagonist αCTLA-4-Fc (SEQ ID NO: 29) by ELISA as described in Example 1. In the ELISA, we found a clear anti-CTLA-4 reactivity for T cells transduced with pSIN-(NFAT)6-αCTLA-4-Fc and cultured under activatory conditions, compared to the mock-transfected cells (FIG. 5). Note that the mock-transfected cells showed a background fluorescence signal due to non-specific matrix effects, which was, however, significantly below the positive ELISA signal of the supernatant of pSIN-(NFAT)6-αCTLA-4-Fc-transduced cells.

TABLE 1

Amino acid SEQ ID NO's in this application and corresponding SEQ ID NO

| Amino acid sequence | DNA sequence |
| --- | --- |
| SEQ ID NO: 1 | SEQ ID NO: 12 |
| SEQ ID NO: 2 | SEQ ID NO: 13 |
| SEQ ID NO: 3 | SEQ ID NO: 14 |
| SEQ ID NO: 4 | SEQ ID NO: 15 |
| SEQ ID NO: 5 | SEQ ID NO: 16 |
| SEQ ID NO: 6 | SEQ ID NO: 17 |
| SEQ ID NO: 7 | SEQ ID NO: 18 |
| SEQ ID NO: 8 | SEQ ID NO: 19 |
| SEQ ID NO: 9 | SEQ ID NO: 20 |
| SEQ ID NO: 10 | SEQ ID NO: 21 |
| SEQ ID NO: 11 | SEQ ID NO: 22 |
| SEQ ID NO: 23 | SEQ ID NO: 24 |
| SEQ ID NO: 25 | SEQ ID NO: 26 |
| SEQ ID NO: 27 | |
| SEQ ID NO: 28 | |
| SEQ ID NO: 29 | |

REFERENCES

Birkholz, K., et al. (2009). "Transfer of mRNA encoding recombinant immunoreceptors reprograms CD4+ and CD8+ T cells for use in the adoptive immunotherapy of cancer." *Gene Ther* 16(5): 596-604.

Brocks, B., et al. (1997). "A TNF receptor antagonistic scFv, which is not secreted in mammalian cells, is expressed as a soluble mono- and bivalent scFv derivative in insect cells." *Immunotechnology* 3(3): 173-84.

Cheadle, E. J., et al. (2012). "Chimeric antigen receptors for T-cell based therapy." Chapter 36, in: "Antibody engineering: methods and protocols", 2nd Edition, Ed. P. Chames, Meth. Mol. Biol. 907, 645-666.

Chen, L., et al. (2013). "Molecular mechanisms of T cell co-stimulation and co-inhibition." *Nat Rev Immunol* 13(4): 227-42.

Chmielewski, M., et al. (2012). "T cells that target carcinoembryonic antigen eradicate orthotopic pancreatic carcinomas without inducing autoimmune colitis in mice." *Gastroenterology* 143(4): 1095-107 e2.

Chmielewski, M., et al. (2011) a. "CD28 cosignalling does not affect the activation threshold in a chimeric antigen receptor-redirected T-cell attack." *Gene Ther* 18(1): 62-72.

Chmielewski, M., et al. (2013) a. "Antigen-Specific T-Cell Activation Independently of the MHC: Chimeric Antigen Receptor-Redirected T Cells." *Front Immunol* 4: 371.

Chmielewski, M., et al. (2014). "Of CARs and TRUCKs: chimeric antigen receptor (CAR) T cells engineered with an inducible cytokine to modulate the tumor stroma." *Immunol Rev* 257(1): 83-90.

Chmielewski, M., et al. (2011) b. "IL-12 release by engineered T cells expressing chimeric antigen receptors can effectively Muster an antigen-independent macrophage response on tumor cells that have shut down tumor antigen expression." *Cancer Res* 71(17): 5697-706.

Chmielewski, M., et al. (2013) b. "T cells redirected by a CD3zeta chimeric antigen receptor can establish self-antigen-specific tumour protection in the long term." *Gene Ther* 20(2): 177-86.

Ewert, S., et al. (2003) a. "Structure-based improvement of the biophysical properties of immunoglobulin VH domains with a generalizable approach." *Biochemistry* 42(6): 1517-28.

Ewert, S., et al. (2003) b. "Biophysical properties of human antibody variable domains." *J Mol Biol* 325(3): 531-53.

Haisma, H. J., et al. (1998) a. "Construction and characterization of a fusion protein of single-chain anti-carcinoma antibody 323/A3 and human beta-glucuronidase." *Cancer Immunol Immunother* 45(5): 266-72.

Haisma, H. J., et al. (1998) b. "Construction and characterization of a fusion protein of single-chain anti-CD20 antibody and human beta-glucuronidase for antibody-directed enzyme prodrug therapy." *Blood* 92(1): 184-90.

Hombach, A., et al. (2010). "Adoptive immunotherapy with genetically engineered T cells: modification of the IgG1 Fc 'spacer' domain in the extracellular moiety of chimeric antigen receptors avoids 'off-target' activation and unintended initiation of an innate immune response." *Gene Ther* 17(10): 1206-13.

Hombach, A. A., et al. (2013). "Arming cytokine-induced killer cells with chimeric antigen receptors: CD28 outperforms combined CD28-OX40 "super-stimulation"." *Mol Ther* 21(12): 2268-77.

Jaalouk, D. E., et al. (2006). "A self-inactivating retrovector incorporating the IL-2 promoter for activation-induced transgene expression in genetically engineered T-cells." *Virol J* 3: 97.

Kershaw, M. H., et al. (2006). "A phase I study on adoptive immunotherapy using gene-modified T cells for ovarian cancer." *Clin Cancer Res* 12(20 Pt 1): 6106-15.

Kofler, D. M., et al. (2011). "CD28 costimulation Impairs the efficacy of a redirected t-cell antitumor attack in the presence of regulatory t cells which can be overcome by preventing Lck activation." *Mol Ther* 19(4): 760-7.

Maiti, S. N., et al. (2013). "Sleeping beauty system to redirect T-cell specificity for human applications." *J Immunother* 36(2): 112-23.

Maliar, A., et al. (2012). "Redirected T cells that target pancreatic adenocarcinoma antigens eliminate tumors and metastases in mice." *Gastroenterology* 143(5): 1375-84 e1-5.

Maude, S. L., et al. (2014). "Chimeric antigen receptor T cells for sustained remissions in leukemia." *N Engl J Med* 371(16): 1507-17.

Pegram, H. J., et al. (2012). "Tumor-targeted T cells modified to secrete IL-12 eradicate systemic tumors without need for prior conditioning." *Blood* 119(18): 4133-41.

Pegram, H. J., et al. (2014). "IL-12-secreting CD19-targeted cord blood-derived T cells for the immunotherapy of B-cell acute lymphoblastic leukemia." *Leukemia*.

Peipp, M., et al. (2004). "Efficient eukaryotic expression of fluorescent scFv fusion proteins directed against CD antigens for FACS applications." *J Immunol Methods* 285(2): 265-80.

Rosenberg, S. A., et al. (1990). "Gene transfer into humans—immunotherapy of patients with advanced melanoma, using tumor-infiltrating lymphocytes modified by retroviral gene transduction." *N Engl J Med* 323(9): 570-8.

Schaefer, J. V., et al. (2012). "Transfer of engineered biophysical properties between different antibody formats and expression systems." *Protein Eng Des Sel* 25(10): 485-506.

Shi, H., et al. (2014). "Chimeric antigen receptor for adoptive immunotherapy of cancer: latest research and future prospects." *Mol Cancer* 13: 219.

Textor, A., et al. (2014). "Efficacy of CAR T-cell Therapy in Large Tumors Relies upon Stromal Targeting by IFN-gamma." *Cancer Res* 74(23): 6796-805.

Weijtens, M. E., et al. (1998). "A retroviral vector system 'STITCH' in combination with an optimized single chain antibody chimeric receptor gene structure allows efficient gene transduction and expression in human T lymphocytes." *Gene Ther* 5(9): 1195-203.

Willemsen, R. A., et al. (2000). "Grafting primary human T lymphocytes with cancer-specific chimeric single chain and two chain TCR." *Gene Ther* 7(16): 1369-77.

Zhang, L., et al. (2011). "Improving adoptive T cell therapy by targeting and controlling IL-12 expression to the tumor environment." *Mol Ther* 19(4): 751-9.

Zhao, Y., et al. (2006). "Transduction of an HLA-DP4-restricted NY-ESO-1-specific TCR into primary human CD4+ lymphocytes." *J Immunother* 29(4): 398-406.

The invention claimed is:

1. A modified T cell expressing and secreting a specific binding polypeptide comprising a mutein of human neutrophil gelatinase-associated lipocalin (hNGAL), wherein the hNGAL mutein is modified such that it is specific for a target other than the natural target of hNGAL, wherein the target other than the natural target is an immunomodulatory target, wherein the hNGAL mutein has at least 96% sequence identity to mature, wild-type hNGAL (SEQ ID NO: 30).

2. A modified T cell expressing and secreting a specific binding polypeptide comprising a lipocalin mutein specific for an immunomodulatory target, wherein the immunomodulatory target is CTLA-4 and the lipocalin mutein comprises the amino acid sequence of SEQ ID NO: 3.

3. The modified T cell of claim 2, wherein the modified T cell comprises a polynucleotide sequence encoding the lipocalin mutein and a secretion signal peptide.

4. A modified T cell expressing and secreting a specific binding polypeptide comprising a lipocalin mutein specific for an immunomodulatory target, wherein the immunomodulatory target is CTLA-4 and the binding polypeptide comprises the amino acid sequence of SEQ ID NO: 28.

5. The modified T cell of claim 4, wherein the binding polypeptide comprises the amino acid sequence of SEQ ID NO: 29.

* * * * *

SEQUENCE LISTING

```
<160> NUMBER OF SEQ ID NOS: 30

<210> SEQ ID NO 1
<211> LENGTH: 152
<212> TYPE: PRT
<213> ORGANISM: artificial
<220> FEATURE:
<223> OTHER INFORMATION: Lipocalin mutein binding c-Met

<400> SEQUENCE: 1

Ala Ser Asp Glu Glu Ile Gln Asp Val Ser Gly Thr Trp Tyr Leu Lys
1               5                   10                  15

Ala Met Thr Val Asp Thr Gln Asp Pro Leu Ser Leu Tyr Val Ser Val
            20                  25                  30
```

```
Ser Pro Ile Thr Leu Thr Thr Leu Glu Gly Gly Asn Leu Glu Ala Thr
            35                  40                  45

Val Thr Leu Asn Gln Ile Gly Arg Ser Gln Glu Val Leu Ala Val Leu
 50                  55                  60

Glu Lys Thr Asp Glu Pro Gly Lys Tyr Thr Leu Tyr Gly Gly Ala His
 65                  70                  75                  80

Val Ala Tyr Ile Gln Arg Ser His Val Lys Asp His Tyr Ile Phe Tyr
                 85                  90                  95

Ser Glu Gly Asp Thr Trp Gly Gly Pro Val Pro Gly Val Trp Leu Val
            100                 105                 110

Gly Arg Asp Pro Lys Asn Asn Leu Glu Ala Leu Glu Asp Phe Glu Lys
            115                 120                 125

Ala Ala Gly Ala Arg Gly Leu Ser Thr Glu Ser Ile Leu Ile Pro Arg
130                 135                 140

Gln Ser Glu Thr Ser Ser Pro Gly
145                 150

<210> SEQ ID NO 2
<211> LENGTH: 178
<212> TYPE: PRT
<213> ORGANISM: artificial
<220> FEATURE:
<223> OTHER INFORMATION: Lipocalin mutein binding GPC-3

<400> SEQUENCE: 2

Gln Asp Ser Thr Ser Asp Leu Ile Pro Ala Pro Pro Leu Ser Lys Val
 1               5                  10                  15

Pro Leu Gln Gln Asn Phe Gln Asp Asn Gln Phe His Gly Lys Trp Tyr
                20                  25                  30

Val Val Gly Arg Ala Gly Asn Val Ala Leu Arg Glu Asp Lys Asp Pro
            35                  40                  45

Pro Lys Met Arg Ala Thr Ile Tyr Glu Leu Lys Glu Asp Lys Ser Tyr
 50                  55                  60

Asn Val Thr Asn Val Arg Phe Ala Met Lys Lys Cys Met Tyr Ser Ile
 65                  70                  75                  80

Gly Thr Phe Val Pro Gly Ser Gln Pro Gly Glu Phe Thr Leu Gly Gln
                 85                  90                  95

Ile Lys Ser Glu Pro Gly Asn Thr Ser Asn Leu Val Arg Val Val Ser
            100                 105                 110

Thr Asn Tyr Asn Gln His Ala Met Val Phe Phe Lys Glu Val Tyr Gln
            115                 120                 125

Asn Arg Glu Ile Phe Phe Ile Thr Leu Tyr Gly Arg Thr Lys Glu Leu
            130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 3
<211> LENGTH: 178
<212> TYPE: PRT
<213> ORGANISM: artificial
<220> FEATURE:
<223> OTHER INFORMATION: Lipocalin mutein binding CTLA-4
```

<400> SEQUENCE: 3

```
Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Arg Ile Leu Arg Gln Asp Gln His Pro
        35                  40                  45

Met Leu Met Tyr Ala Thr Ile Tyr Glu Leu Lys Glu Asp Lys Ser Tyr
    50                  55                  60

Gln Val Thr Ser Val Ile Ser Ser His Lys Lys Cys Leu Tyr Pro Ile
65                  70                  75                  80

Ala Thr Phe Val Pro Gly Ser Gln Pro Gly Glu Phe Thr Leu Gly Asn
                85                  90                  95

Ile Lys Ser Tyr Gly Asp Lys Val Ser Tyr Leu Val Arg Val Val Ser
            100                 105                 110

Thr Asn Tyr Asn Gln His Ala Met Val Phe Phe Lys His Ala Asp Thr
        115                 120                 125

Asn Tyr Glu Ser Phe Ser Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly
```

<210> SEQ ID NO 4
<211> LENGTH: 69
<212> TYPE: PRT
<213> ORGANISM: artificial
<220> FEATURE:
<223> OTHER INFORMATION: CD8 linker and transmembrane region

<400> SEQUENCE: 4

```
Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile Tyr Ile
        35                  40                  45

Trp Ala Pro Leu Ala Gly Thr Cys Gly Val Leu Leu Leu Ser Leu Val
    50                  55                  60

Ile Thr Leu Tyr Cys
65
```

<210> SEQ ID NO 5
<211> LENGTH: 113
<212> TYPE: PRT
<213> ORGANISM: artificial
<220> FEATURE:
<223> OTHER INFORMATION: intracellular signaling domain of CD3zeta

<400> SEQUENCE: 5

```
Leu Arg Val Lys Phe Ser Arg Ser Ala Asp Ala Pro Ala Tyr Lys Gln
1               5                   10                  15

Gly Gln Asn Gln Leu Tyr Asn Glu Leu Asn Leu Gly Arg Arg Glu Glu
            20                  25                  30
```

```
Tyr Asp Val Leu Asp Lys Arg Arg Gly Arg Asp Pro Glu Met Gly Gly
             35                  40                  45

Lys Pro Arg Arg Lys Asn Pro Gln Glu Gly Leu Tyr Asn Glu Leu Gln
 50                      55                  60

Lys Asp Lys Met Ala Glu Ala Tyr Ser Glu Ile Gly Met Lys Gly Glu
 65                  70                  75                  80

Arg Arg Arg Gly Lys Gly His Asp Gly Leu Tyr Gln Gly Leu Ser Thr
                 85                  90                  95

Ala Thr Lys Asp Thr Tyr Asp Ala Leu His Met Gln Ala Leu Pro Pro
            100                 105                 110

Arg

<210> SEQ ID NO 6
<211> LENGTH: 44
<212> TYPE: PRT
<213> ORGANISM: artificial
<220> FEATURE:
<223> OTHER INFORMATION: intracellular signaling domain of CD28

<400> SEQUENCE: 6

Phe Trp Val Arg Ser Lys Arg Ser Arg Leu Leu His Ser Asp Tyr Met
 1               5                  10                  15

Asn Met Thr Pro Arg Arg Pro Gly Pro Thr Arg Lys His Tyr Gln Pro
             20                  25                  30

Tyr Ala Pro Pro Arg Asp Phe Ala Ala Tyr Arg Ser
             35                  40

<210> SEQ ID NO 7
<211> LENGTH: 41
<212> TYPE: PRT
<213> ORGANISM: artificial
<220> FEATURE:
<223> OTHER INFORMATION: intracellular signaling domain of CD137

<400> SEQUENCE: 7

Lys Arg Gly Arg Lys Lys Leu Leu Tyr Ile Phe Lys Gln Pro Phe Met
 1               5                  10                  15

Arg Pro Val Gln Thr Thr Gln Glu Glu Asp Gly Cys Ser Cys Arg Phe
             20                  25                  30

Pro Glu Glu Glu Glu Gly Gly Cys Glu
             35                  40

<210> SEQ ID NO 8
<211> LENGTH: 378
<212> TYPE: PRT
<213> ORGANISM: artificial
<220> FEATURE:
<223> OTHER INFORMATION: c-Met-CD28-CD3zeta polypeptide

<400> SEQUENCE: 8

Ala Ser Asp Glu Glu Ile Gln Asp Val Ser Gly Thr Trp Tyr Leu Lys
 1               5                  10                  15

Ala Met Thr Val Asp Thr Gln Asp Pro Leu Ser Leu Tyr Val Ser Val
             20                  25                  30

Ser Pro Ile Thr Leu Thr Thr Leu Glu Gly Gly Asn Leu Glu Ala Thr
             35                  40                  45

Val Thr Leu Asn Gln Ile Gly Arg Ser Gln Glu Val Leu Ala Val Leu
 50                  55                  60

Glu Lys Thr Asp Glu Pro Gly Lys Tyr Thr Leu Tyr Gly Gly Ala His
 65                  70                  75                  80
```

```
Val Ala Tyr Ile Gln Arg Ser His Val Lys Asp His Tyr Ile Phe Tyr
            85                  90                  95

Ser Glu Gly Asp Thr Trp Gly Gly Pro Val Pro Gly Val Trp Leu Val
        100                 105                 110

Gly Arg Asp Pro Lys Asn Asn Leu Glu Ala Leu Glu Asp Phe Glu Lys
    115                 120                 125

Ala Ala Gly Ala Arg Gly Leu Ser Thr Glu Ser Ile Leu Ile Pro Arg
130                 135                 140

Gln Ser Glu Thr Ser Ser Pro Gly Thr Thr Pro Ala Pro Arg Pro
145                 150                 155                 160

Pro Thr Pro Ala Pro Thr Ile Ala Ser Gln Pro Leu Ser Leu Arg Pro
                165                 170                 175

Glu Ala Cys Arg Pro Ala Ala Gly Gly Ala Val His Thr Arg Gly Leu
            180                 185                 190

Asp Phe Ala Cys Asp Ile Tyr Ile Trp Ala Pro Leu Ala Gly Thr Cys
        195                 200                 205

Gly Val Leu Leu Leu Ser Leu Val Ile Thr Leu Tyr Cys Phe Trp Val
    210                 215                 220

Arg Ser Lys Arg Ser Arg Leu Leu His Ser Asp Tyr Met Asn Met Thr
225                 230                 235                 240

Pro Arg Arg Pro Gly Pro Thr Arg Lys His Tyr Gln Pro Tyr Ala Pro
                245                 250                 255

Pro Arg Asp Phe Ala Ala Tyr Arg Ser Leu Arg Val Lys Phe Ser Arg
            260                 265                 270

Ser Ala Asp Ala Pro Ala Tyr Lys Gln Gly Gln Asn Gln Leu Tyr Asn
        275                 280                 285

Glu Leu Asn Leu Gly Arg Arg Glu Glu Tyr Asp Val Leu Asp Lys Arg
    290                 295                 300

Arg Gly Arg Asp Pro Glu Met Gly Gly Lys Pro Arg Arg Lys Asn Pro
305                 310                 315                 320

Gln Glu Gly Leu Tyr Asn Glu Leu Gln Lys Asp Lys Met Ala Glu Ala
                325                 330                 335

Tyr Ser Glu Ile Gly Met Lys Gly Glu Arg Arg Arg Gly Lys Gly His
            340                 345                 350

Asp Gly Leu Tyr Gln Gly Leu Ser Thr Ala Thr Lys Asp Thr Tyr Asp
        355                 360                 365

Ala Leu His Met Gln Ala Leu Pro Pro Arg
    370                 375

<210> SEQ ID NO 9
<211> LENGTH: 375
<212> TYPE: PRT
<213> ORGANISM: artificial
<220> FEATURE:
<223> OTHER INFORMATION: c-Met-CD137-CD3zeta polypeptide

<400> SEQUENCE: 9

Ala Ser Asp Glu Glu Ile Gln Asp Val Ser Gly Thr Trp Tyr Leu Lys
1               5                   10                  15

Ala Met Thr Val Asp Thr Gln Asp Pro Leu Ser Leu Tyr Val Ser Val
            20                  25                  30

Ser Pro Ile Thr Leu Thr Thr Leu Glu Gly Gly Asn Leu Glu Ala Thr
        35                  40                  45

Val Thr Leu Asn Gln Ile Gly Arg Ser Gln Glu Val Leu Ala Val Leu
    50                  55                  60

Glu Lys Thr Asp Glu Pro Gly Lys Tyr Thr Leu Tyr Gly Gly Ala His
```

```
                65                  70                  75                  80
Val Ala Tyr Ile Gln Arg Ser His Val Lys Asp His Tyr Ile Phe Tyr
                    85                  90                  95

Ser Glu Gly Asp Thr Trp Gly Gly Pro Val Pro Gly Val Trp Leu Val
                100                 105                 110

Gly Arg Asp Pro Lys Asn Asn Leu Glu Ala Leu Glu Asp Phe Glu Lys
                115                 120                 125

Ala Ala Gly Ala Arg Gly Leu Ser Thr Glu Ser Ile Leu Ile Pro Arg
        130                 135                 140

Gln Ser Glu Thr Ser Ser Pro Gly Thr Thr Pro Ala Pro Arg Pro
145                 150                 155                 160

Pro Thr Pro Ala Pro Thr Ile Ala Ser Gln Pro Leu Ser Leu Arg Pro
                165                 170                 175

Glu Ala Cys Arg Pro Ala Ala Gly Gly Ala Val His Thr Arg Gly Leu
                180                 185                 190

Asp Phe Ala Cys Asp Ile Tyr Ile Trp Ala Pro Leu Ala Gly Thr Cys
                195                 200                 205

Gly Val Leu Leu Leu Ser Leu Val Ile Thr Leu Tyr Cys Lys Arg Gly
        210                 215                 220

Arg Lys Lys Leu Leu Tyr Ile Phe Lys Gln Pro Phe Met Arg Pro Val
225                 230                 235                 240

Gln Thr Thr Gln Glu Glu Asp Gly Cys Ser Cys Arg Phe Pro Glu Glu
                245                 250                 255

Glu Glu Gly Gly Cys Glu Leu Arg Val Lys Phe Ser Arg Ser Ala Asp
                260                 265                 270

Ala Pro Ala Tyr Lys Gln Gly Gln Asn Gln Leu Tyr Asn Glu Leu Asn
        275                 280                 285

Leu Gly Arg Arg Glu Glu Tyr Asp Val Leu Asp Lys Arg Arg Gly Arg
        290                 295                 300

Asp Pro Glu Met Gly Gly Lys Pro Arg Arg Lys Asn Pro Gln Glu Gly
305                 310                 315                 320

Leu Tyr Asn Glu Leu Gln Lys Asp Lys Met Ala Glu Ala Tyr Ser Glu
                325                 330                 335

Ile Gly Met Lys Gly Glu Arg Arg Arg Gly Lys Gly His Asp Gly Leu
                340                 345                 350

Tyr Gln Gly Leu Ser Thr Ala Thr Lys Asp Thr Tyr Asp Ala Leu His
        355                 360                 365

Met Gln Ala Leu Pro Pro Arg
    370                 375

<210> SEQ ID NO 10
<211> LENGTH: 404
<212> TYPE: PRT
<213> ORGANISM: artificial
<220> FEATURE:
<223> OTHER INFORMATION: GPC3-CD28-CD3zeta polypeptide

<400> SEQUENCE: 10

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
                20                  25                  30

Val Val Gly Arg Ala Gly Asn Val Ala Leu Arg Glu Asp Lys Asp Pro
        35                  40                  45
Pro Lys Met Arg Ala Thr Ile Tyr Glu Leu Lys Glu Asp Lys Ser Tyr
    50                  55                  60
```

```
Asn Val Thr Asn Val Arg Phe Ala Met Lys Lys Cys Met Tyr Ser Ile
 65                  70                  75                  80

Gly Thr Phe Val Pro Gly Ser Gln Pro Gly Glu Phe Thr Leu Gly Gln
                 85                  90                  95

Ile Lys Ser Glu Pro Gly Asn Thr Ser Asn Leu Val Arg Val Val Ser
            100                 105                 110

Thr Asn Tyr Asn Gln His Ala Met Val Phe Phe Lys Glu Val Tyr Gln
            115                 120                 125

Asn Arg Glu Ile Phe Phe Ile Thr Leu Tyr Gly Arg Thr Lys Glu Leu
            130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Thr Thr Thr Pro Ala Pro Arg Pro Pro Thr Pro Ala Pro Thr
            180                 185                 190

Ile Ala Ser Gln Pro Leu Ser Leu Arg Pro Glu Ala Cys Arg Pro Ala
            195                 200                 205

Ala Gly Gly Ala Val His Thr Arg Gly Leu Asp Phe Ala Cys Asp Ile
            210                 215                 220

Tyr Ile Trp Ala Pro Leu Ala Gly Thr Cys Gly Val Leu Leu Leu Ser
225                 230                 235                 240

Leu Val Ile Thr Leu Tyr Cys Phe Trp Val Arg Ser Lys Arg Ser Arg
                245                 250                 255

Leu Leu His Ser Asp Tyr Met Asn Met Thr Pro Arg Arg Pro Gly Pro
            260                 265                 270

Thr Arg Lys His Tyr Gln Pro Tyr Ala Pro Pro Arg Asp Phe Ala Ala
            275                 280                 285

Tyr Arg Ser Leu Arg Val Lys Phe Ser Arg Ser Ala Asp Ala Pro Ala
            290                 295                 300

Tyr Lys Gln Gly Gln Asn Gln Leu Tyr Asn Glu Leu Asn Leu Gly Arg
305                 310                 315                 320

Arg Glu Glu Tyr Asp Val Leu Asp Lys Arg Arg Gly Arg Asp Pro Glu
                325                 330                 335

Met Gly Gly Lys Pro Arg Arg Lys Asn Pro Gln Glu Gly Leu Tyr Asn
            340                 345                 350

Glu Leu Gln Lys Asp Lys Met Ala Glu Ala Tyr Ser Glu Ile Gly Met
            355                 360                 365

Lys Gly Glu Arg Arg Arg Gly Lys Gly His Asp Gly Leu Tyr Gln Gly
            370                 375                 380

Leu Ser Thr Ala Thr Lys Asp Thr Tyr Asp Ala Leu His Met Gln Ala
385                 390                 395                 400

Leu Pro Pro Arg

<210> SEQ ID NO 11
<211> LENGTH: 401
<212> TYPE: PRT
<213> ORGANISM: artificial
<220> FEATURE:
<223> OTHER INFORMATION: GPC3-CD137-CD3zeta polypeptide
```

```
<400> SEQUENCE: 11

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Arg Ala Gly Asn Val Ala Leu Arg Glu Asp Lys Asp Pro
        35                  40                  45

Pro Lys Met Arg Ala Thr Ile Tyr Glu Leu Lys Glu Asp Lys Ser Tyr
    50                  55                  60

Asn Val Thr Asn Val Arg Phe Ala Met Lys Lys Cys Met Tyr Ser Ile
65                  70                  75                  80

Gly Thr Phe Val Pro Gly Ser Gln Pro Gly Glu Phe Thr Leu Gly Gln
                85                  90                  95

Ile Lys Ser Glu Pro Gly Asn Thr Ser Asn Leu Val Arg Val Val Ser
            100                 105                 110

Thr Asn Tyr Asn Gln His Ala Met Val Phe Phe Lys Glu Val Tyr Gln
            115                 120                 125

Asn Arg Glu Ile Phe Phe Ile Thr Leu Tyr Gly Arg Thr Lys Glu Leu
130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Thr Thr Thr Pro Ala Pro Arg Pro Pro Thr Pro Ala Pro Thr
            180                 185                 190

Ile Ala Ser Gln Pro Leu Ser Leu Arg Pro Glu Ala Cys Arg Pro Ala
            195                 200                 205

Ala Gly Gly Ala Val His Thr Arg Gly Leu Asp Phe Ala Cys Asp Ile
210                 215                 220

Tyr Ile Trp Ala Pro Leu Ala Gly Thr Cys Gly Val Leu Leu Leu Ser
225                 230                 235                 240

Leu Val Ile Thr Leu Tyr Cys Lys Arg Gly Arg Lys Lys Leu Leu Tyr
                245                 250                 255

Ile Phe Lys Gln Pro Phe Met Arg Pro Val Gln Thr Thr Gln Glu Glu
            260                 265                 270

Asp Gly Cys Ser Cys Arg Phe Pro Glu Glu Glu Glu Gly Gly Cys Glu
            275                 280                 285

Leu Arg Val Lys Phe Ser Arg Ser Ala Asp Ala Pro Ala Tyr Lys Gln
290                 295                 300

Gly Gln Asn Gln Leu Tyr Asn Glu Leu Asn Leu Gly Arg Arg Glu Glu
305                 310                 315                 320

Tyr Asp Val Leu Asp Lys Arg Gly Arg Asp Pro Glu Met Gly Gly
                325                 330                 335

Lys Pro Arg Arg Lys Asn Pro Gln Glu Gly Leu Tyr Asn Glu Leu Gln
            340                 345                 350

Lys Asp Lys Met Ala Glu Ala Tyr Ser Glu Ile Gly Met Lys Gly Glu
            355                 360                 365

Arg Arg Arg Gly Lys Gly His Asp Gly Leu Tyr Gln Gly Leu Ser Thr
370                 375                 380

Ala Thr Lys Asp Thr Tyr Asp Ala Leu His Met Gln Ala Leu Pro Pro
385                 390                 395                 400

Arg

<210> SEQ ID NO 12
```

```
<211> LENGTH: 456
<212> TYPE: DNA
<213> ORGANISM: artificial
<220> FEATURE:
<223> OTHER INFORMATION: nucleotide sequence encoding amino acid
      sequence of SEQ ID NO: 1

<400> SEQUENCE: 12
gcttctgatg aagaaatcca ggatgtgtct ggcacctggt acctgaaggc tatgaccgtg      60
gatacccagg atccgctgtc tctgtacgtg tctgtgtctc cgatcaccct gaccaccctg     120
gaaggcggca acctggaagc taccgtgacc ctgaaccaga tcggccgttc tcaggaagtg     180
ctggctgtgc tggaaaagac cgatgaaccg gcaagtaca cccgtacgg cggcgctcat      240 gtggcttaca tccagcgttc tcatgtgaag gatcattaca tcttctactc tgaaggcgat     300
acctggggcg cccggtgcc gggcgtgtgg ctggtgggcc gtgatccgaa gaacaacctg     360
gaagctctgg aagatttcga aaaggctgct ggcgctcgtg gcctgtctac cgaatctatc     420
ctgatcccgc gtcagtctga aacctcttct ccgggc                              456

<210> SEQ ID NO 13
<211> LENGTH: 534
<212> TYPE: DNA
<213> ORGANISM: artificial
<220> FEATURE:
<223> OTHER INFORMATION: nucleotide sequence encoding amino acid
      sequence of SEQ ID NO: 2

<400> SEQUENCE: 13
caggattcta cctctgatct gatcccggct ccgccgctgt ctaaggtgcc gctgcagcag      60
aacttccagg ataaccagtt ccatggcaag tggtacgtgg tgggccgtgc tggcaacgtg     120
gctctgcgtg aagataagga tccgccgaag atgcgtgcta ccatctacga actgaaggaa     180
gataagtctt acaacgtgac caacgtgcgt ttcgctatga gaagtgcat gtactctatc     240 ggcaccttcg tgccgggctc tcagccgggc gaattcaccc tgggccagat caagtctgaa     300
ccgggcaaca cctctaacct ggtgcgtgtg gtgtctacca actacaacca gcatgctatg     360
gtgttcttca aggaagtgta ccagaaccgt gaaatcttct tcatcaccct gtacggccgt     420
accaaggaac tgacctctga actgaaggaa aacttcatcc gtttctctaa gtctctgggc     480
ctgccggaaa accatatcgt gttcccggtg ccgatcgatc agtgcatcga tggc          534

<210> SEQ ID NO 14
<211> LENGTH: 534
<212> TYPE: DNA
<213> ORGANISM: artificial
<220> FEATURE:
<223> OTHER INFORMATION: nucleotide sequence encoding amino acid
      sequence of SEQ ID NO: 3

<400> SEQUENCE: 14
caggattcta cctctgatct gatcccggct ccgccgctgt ctaaggtgcc gctgcagcag      60
aacttccagg ataaccagtt ccagggcaag tggtacgtgg tgggcctggc tggcaaccgt     120
atcctgcgtc aggatcagca tccgatgctg atgtacgcta ccatctacga actgaaggaa     180
gataagtctt accaggtgac ctctgtgatc tcttctcata gaagtgcct gtaccgatc      240 gctaccttcg tgccgggctc tcagccgggc gaattcaccc tgggcaacat caagtcttac     300
ggcgataagg tgtcttacct ggtgcgtgtg gtgtctacca actacaacca gcatgctatg     360
gtgttcttca agcatgctga taccaactac gaatctttct ctatcaccct gtacggccgt     420
```

```
accaaggaac tgacctctga actgaaggaa aacttcatcc gtttctctaa gtctctgggc      480
ctgccggaaa accatatcgt gttcccggtg ccgatcgatc agtgcatcga tggc            534
```

```
<210> SEQ ID NO 15
<211> LENGTH: 207
<212> TYPE: DNA
<213> ORGANISM: artificial
<220> FEATURE:
<223> OTHER INFORMATION: nucleotide sequence encoding amino acid
      sequence of SEQ ID NO: 4

<400> SEQUENCE: 15
accaccaccc cggctccgcg tccgccgacc ccggctccga ccatcgcttc tcagccgctg       60
tctctgcgtc cggaagcttg ccgtccggct gctggcggcg ctgtgcatac cgtggcctg      120 gatttcgctt gcgatatcta catctgggct ccgctggctg gcacctgcgg cgtgctgctg    180
ctgtctctgg tgatcaccct gtactgc                                         207
```

```
<210> SEQ ID NO 16
<211> LENGTH: 339
<212> TYPE: DNA
<213> ORGANISM: artificial
<220> FEATURE:
<223> OTHER INFORMATION: nucleotide sequence encoding amino acid
      sequence of SEQ ID NO: 5

<400> SEQUENCE: 16
ctgcgtgtga agttctctcg ttctgctgat gctccggctt acaagcaggg ccagaaccag       60
ctgtacaacg aactgaacct gggccgtcgt gaagaataca tgtgctgga taagcgtcgt      120 ggccgtgatc cggaaatggg cggcaagccg cgtcgtaaga acccgcagga aggcctgtac    180
aacgaactgc agaaggataa gatggctgaa gcttactctg aaatcggcat gaagggcgaa    240
cgtcgtcgtg caagggccca tgatggcctg taccagggcc tgtctaccgc taccaaggat    300
acctacgatg ctctgcatat gcaggctctg ccgccgcgt                            339
```

```
<210> SEQ ID NO 17
<211> LENGTH: 132
<212> TYPE: DNA
<213> ORGANISM: artificial
<220> FEATURE:
<223> OTHER INFORMATION: nucleotide sequence encoding amino acid
      sequence of SEQ ID NO: 6

<400> SEQUENCE: 17
ttctgggtgc gttctaagcg ttctcgtctg ctgcattctg attacatgaa catgaccccg       60
cgtcgtccgg gcccgacccg taagcattac cagccgtacg ctccgccgcg tgatttcgct    120
gcttaccgtt ct                                                         132
```

```
<210> SEQ ID NO 18
<211> LENGTH: 123
<212> TYPE: DNA
<213> ORGANISM: artificial
<220> FEATURE:
<223> OTHER INFORMATION: nucleotide sequence encoding amino acid
      sequence of SEQ ID NO: 7

<400> SEQUENCE: 18
aagcgtggcc gtaagaagct gctgtacatc ttcaagcagc cgttcatgcg tccggtgcag       60
accacccagg aagaagatgg ctgctcttgc cgtttccgg aagaagaaga aggcggctgc      120
gaa                                                                   123
```

<210> SEQ ID NO 19
<211> LENGTH: 1134
<212> TYPE: DNA
<213> ORGANISM: artificial
<220> FEATURE:
<223> OTHER INFORMATION: nucleotide sequence encoding amino acid
      sequence of SEQ ID NO: 8

<400> SEQUENCE: 19

| | | | | | | |
|---|---|---|---|---|---|---|
| gcttctgatg | aagaaatcca | ggatgtgtct | ggcacctggt | acctgaaggc | tatgaccgtg | 60 |
| gatacccagg | atccgctgtc | tctgtacgtg | tctgtgtctc | cgatcaccct | gaccaccctg | 120 |
| gaaggcggca | acctggaagc | taccgtgacc | ctgaaccaga | tcggccgttc | tcaggaagtg | 180 |
| ctggctgtgc | tggaaaagac | cgatgaaccg | ggcaagtaca | ccctgtacgg | cggcgctcat | 240 |
| gtggcttaca | tccagcgttc | tcatgtgaag | gatcattaca | tcttctactc | tgaaggcgat | 300 |
| acctggggcg | gcccggtgcc | gggcgtgtgg | ctggtgggcc | gtgatccgaa | gaacaacctg | 360 |
| gaagctctgg | aagatttcga | aaaggctgct | ggcgctcgtg | gcctgtctac | cgaatctatc | 420 |
| ctgatcccgc | gtcagtctga | aacctcttct | ccgggcacca | ccaccccggc | tccgcgtccg | 480 |
| ccgacccggg | ctccgaccat | cgcttctcag | ccgctgtctc | tgcgtccgga | agcttgccgt | 540 |
| ccggctgctg | gcggcgctgt | gcatacccgt | ggcctggatt | tcgcttgcga | tatctacatc | 600 |
| tgggctccgc | tggctggcac | ctgcggcgtg | ctgctgctgt | ctctggtgat | caccctgtac | 660 |
| tgcttctggg | tgcgttctaa | cgttctcgt | ctgctgcatt | ctgattacat | gaacatgacc | 720 |
| ccgcgtcgtc | cgggcccgac | ccgtaagcat | accagccgt | acgctccgcc | gcgtgatttc | 780 |
| gctgcttacc | gttctctgcg | tgtgaagttc | tctcgttctg | ctgatgctcc | ggcttacaag | 840 |
| cagggccaga | ccagctgta | caacgaactg | aacctgggcc | gtcgtgaaga | atacgatgtg | 900 |
| ctggataagc | gtcgtggccg | tgatccggaa | atgggcggca | agccgcgtcg | taagaacccg | 960 |
| caggaaggcc | tgtacaacga | actgcagaag | gataagatgg | ctgaagctta | ctctgaaatc | 1020 |
| ggcatgaagg | gcgaacgtcg | tcgtggcaag | ggccatgatg | gcctgtacca | gggcctgtct | 1080 |
| accgctacca | aggatacccta | cgatgctctg | catatgcagg | ctctgccgcc | gcgt | 1134 |

<210> SEQ ID NO 20
<211> LENGTH: 1125
<212> TYPE: DNA
<213> ORGANISM: artificial
<220> FEATURE:
<223> OTHER INFORMATION: nucleotide sequence encoding amino acid
      sequence of SEQ ID NO: 9

<400> SEQUENCE: 20

| | | | | | | |
|---|---|---|---|---|---|---|
| gcttctgatg | aagaaatcca | ggatgtgtct | ggcacctggt | acctgaaggc | tatgaccgtg | 60 |
| gatacccagg | atccgctgtc | tctgtacgtg | tctgtgtctc | cgatcaccct | gaccaccctg | 120 |
| gaaggcggca | acctggaagc | taccgtgacc | ctgaaccaga | tcggccgttc | tcaggaagtg | 180 |
| ctggctgtgc | tggaaaagac | cgatgaaccg | ggcaagtaca | ccctgtacgg | cggcgctcat | 240 |
| gtggcttaca | tccagcgttc | tcatgtgaag | gatcattaca | tcttctactc | tgaaggcgat | 300 |
| acctggggcg | gcccggtgcc | gggcgtgtgg | ctggtgggcc | gtgatccgaa | gaacaacctg | 360 |
| gaagctctgg | aagatttcga | aaaggctgct | ggcgctcgtg | gcctgtctac | cgaatctatc | 420 |
| ctgatcccgc | gtcagtctga | aacctcttct | ccgggcacca | ccaccccggc | tccgcgtccg | 480 |
| ccgacccggg | ctccgaccat | cgcttctcag | ccgctgtctc | tgcgtccgga | agcttgccgt | 540 |
| ccggctgctg | gcggcgctgt | gcatacccgt | ggcctggatt | tcgcttgcga | tatctacatc | 600 |

-continued

| | |
|---|---|
| tgggctccgc tggctggcac ctgcggcgtg ctgctgctgt ctctggtgat caccctgtac | 660 |
| tgcaagcgtg gccgtaagaa gctgctgtac atcttcaagc agccgttcat gcgtccggtg | 720 |
| cagaccaccc aggaagaaga tggctgctct tgccgtttcc ggaagaaga agaaggcggc | 780 |
| tgcgaactgc gtgtgaagtt ctctcgttct gctgatgctc cggcttacaa gcagggccag | 840 |
| aaccagctgt acaacgaact gaacctgggc cgtcgtgaag aatacgatgt gctggataag | 900 |
| cgtcgtggcc gtgatccgga aatgggcggc aagccgcgtc gtaagaaccc gcaggaaggc | 960 |
| ctgtacaacg aactgcagaa ggataagatg gctgaagctt actctgaaat cggcatgaag | 1020 |
| ggcgaacgtc gtcgtggcaa gggccatgat ggcctgtacc agggcctgtc taccgctacc | 1080 |
| aaggatacct acgatgctct gcatatgcag gctctgccgc cgcgt | 1125 |

<210> SEQ ID NO 21
<211> LENGTH: 1212
<212> TYPE: DNA
<213> ORGANISM: artificial
<220> FEATURE:
<223> OTHER INFORMATION: nucleotide sequence encoding amino acid
      sequence of SEQ ID NO: 10

<400> SEQUENCE: 21

| | |
|---|---|
| caggattcta cctctgatct gatcccggct ccgccgctgt ctaaggtgcc gctgcagcag | 60 |
| aacttccagg ataaccagtt ccatggcaag tggtacgtgg tgggccgtgc tggcaacgtg | 120 |
| gctctgcgtg aagataagga tccgccgaag atgcgtgcta ccatctacga actgaaggaa | 180 |
| gataagtctt acaacgtgac caacgtgcgt ttcgctatga gaagtgcat gtactctatc | 240 |
| ggcaccttcg tgccgggctc tcagccgggc gaattcaccc tgggccagat caagtctgaa | 300 |
| ccgggcaaca cctctaacct ggtgcgtgtg tgtctacca actacaacca gcatgctatg | 360 |
| gtgttcttca aggaagtgta ccagaaccgt gaaatcttct tcatcaccct gtacggccgt | 420 |
| accaaggaac tgacctctga actgaaggaa aacttcatcc gtttctctaa gtctctgggc | 480 |
| ctgccggaaa accatatcgt gttcccggtg ccgatcgatc agtgcatcga tggcaccacc | 540 |
| accccggctc cgcgtccgcc gacccggct ccgaccatcg cttctcagcc gctgtctctg | 600 |
| cgtccggaag cttgccgtcc ggctgctggc ggcgctgtgc atacccgtgg cctggatttc | 660 |
| gcttgcgata tctacatctg ggctccgctg gctggcacct cggcgtgct gctgctgtct | 720 |
| ctggtgatca ccctgtactg cttctgggtg cgttctaagc gttctcgtct gctgcattct | 780 |
| gattacatga acatgacccc gcgtcgtccg ggccccgaccc gtaagcatta ccagccgtac | 840 |
| gctccgccgc gtgatttcgc tgcttaccgt tctctgcgtg tgaagttctc tcgttctgct | 900 |
| gatgctccgg cttacaagca gggccagaac cagctgtaca acgaactgaa cctgggccgt | 960 |
| cgtgaagaat acgatgtgct ggataagcgt cgtggccgtg atccggaaat gggcggcaag | 1020 |
| ccgcgtcgta agaacccgca ggaaggcctg tacaacgaac tgcagaagga taagatggct | 1080 |
| gaagcttact ctgaaatcgg catgaagggc gaacgtcgtc gtggcaaggg ccatgatggc | 1140 |
| ctgtaccagg gcctgtctac cgctaccaag gatacctacg atgctctgca tatgcaggct | 1200 |
| ctgccgccgc gt | 1212 |

<210> SEQ ID NO 22
<211> LENGTH: 1203
<212> TYPE: DNA
<213> ORGANISM: artificial
<220> FEATURE:
<223> OTHER INFORMATION: nucleotide sequence encoding amino acid
      sequence of SEQ ID NO: 11

-continued

```
<400> SEQUENCE: 22
caggattcta cctctgatct gatcccggct ccgccgctgt ctaaggtgcc gctgcagcag        60
aacttccagg ataaccagtt ccatggcaag tggtacgtgg tgggccgtgc tggcaacgtg       120
gctctgcgtg aagataagga tccgccgaag atgcgtgcta ccatctacga actgaaggaa       180
gataagtctt acaacgtgac caacgtgcgt ttcgctatga agaagtgcat gtactctatc       240
ggcaccttcg tgccgggctc tcagccgggc gaattcaccc tgggccagat caagtctgaa       300
ccgggcaaca cctctaacct ggtgcgtgtg gtgtctacca actacaacca gcatgctatg       360
gtgttcttca aggaagtgta ccagaaccgt gaaatcttct tcatcaccct gtacggccgt       420
accaaggaac tgacctctga actgaaggaa aacttcatcc gtttctctaa gtctctgggc       480
ctgccggaaa accatatcgt gttcccggtg ccgatcgatc agtgcatcga tgcaccacc        540
accccggctc cgcgtccgcc gacccggct ccgaccatcg cttctcagcc gctgtctctg        600
cgtccggaag cttgccgtcc ggctgctggc ggcgctgtgc atacccgtgg cctggatttc       660
gcttgcgata tctacatctg ggctccgctg ctggcacct gcggcgtgct gctgctgtct        720
ctggtgatca ccctgtactg caagcgtggc cgtaagaagc tgctgtacat cttcaagcag       780
ccgttcatgc gtccggtgca gaccacccag gaagaagatg gctgctcttg ccgtttcccg       840
gaagaagaag aaggcggctg cgaactgcgt gtgaagttct ctcgttctgc tgatgctccg       900
gcttacaagc agggccagaa ccagctgtac aacgaactga acctgggccg tcgtgaagaa       960
tacgatgtgc tggataagcg tcgtggccgt gatccggaaa tgggcggcaa gccgcgtcgt      1020
aagaacccgc aggaaggcct gtacaacgaa ctgcagaagg ataagatggc tgaagcttac      1080
tctgaaatcg gcatgaaggg cgaacgtcgt cgtggcaagg ccatgatgg cctgtaccag       1140
ggcctgtcta ccgctaccaa ggatacctac gatgctctgc atatgcaggc tctgccgccg      1200
cgt                                                                     1203
```

<210> SEQ ID NO 23
<211> LENGTH: 209
<212> TYPE: PRT
<213> ORGANISM: artificial
<220> FEATURE:
<223> OTHER INFORMATION: secreted anti-CTLA-4 antagonist

<400> SEQUENCE: 23

```
Met Asp Phe Gln Val Gln Ile Phe Ser Phe Leu Leu Ile Ser Ala Ser
 1               5                  10                  15

Val Ile Met Ser Arg Gln Asp Ser Thr Ser Asp Leu Ile Pro Ala Pro
            20                  25                  30

Pro Leu Ser Lys Val Pro Leu Gln Gln Asn Phe Gln Asp Asn Gln Phe
        35                  40                  45

Gln Gly Lys Trp Tyr Val Val Gly Leu Ala Gly Asn Arg Ile Leu Arg
    50                  55                  60

Gln Asp Gln His Pro Met Leu Met Tyr Ala Thr Ile Tyr Glu Leu Lys
65                  70                  75                  80

Glu Asp Lys Ser Tyr Gln Val Thr Ser Val Ile Ser Ser His Lys Lys
                85                  90                  95

Cys Leu Tyr Pro Ile Ala Thr Phe Val Pro Gly Ser Gln Pro Gly Glu
            100                 105                 110

Phe Thr Leu Gly Asn Ile Lys Ser Tyr Gly Asp Lys Val Ser Tyr Leu
        115                 120                 125
```

Val Arg Val Val Ser Thr Asn Tyr Asn Gln His Ala Met Val Phe Phe
            130                 135                 140

Lys His Ala Asp Thr Asn Tyr Glu Ser Phe Ser Ile Thr Leu Tyr Gly
145                 150                 155                 160

Arg Thr Lys Glu Leu Thr Ser Glu Leu Lys Glu Asn Phe Ile Arg Phe
                165                 170                 175

Ser Lys Ser Leu Gly Leu Pro Glu Asn His Ile Val Phe Pro Val Pro
            180                 185                 190

Ile Asp Gln Cys Ile Asp Gly Ser Ala Trp Ser His Pro Gln Phe Glu
        195                 200                 205

Lys

<210> SEQ ID NO 24
<211> LENGTH: 630
<212> TYPE: DNA
<213> ORGANISM: artificial
<220> FEATURE:
<223> OTHER INFORMATION: nucleotide sequence encoding the amino acid
      sequence of SEQ ID NO: 23

<400> SEQUENCE: 24
atggattttc aggtgcagat tttcagcttc ctgctaatca gtgcctcagt cataatgtct      60
agacaggact ccacctctga tctcatcccc gcacctccgc ttagcaaggt tcccttgcaa     120
cagaattttc aggacaatca attccagggg aaatggtacg tagtgggct cgccggcaac     180 agaatcctga gacaagacca gcacccaatg ctgatgtacg ctacgatcta cgagttgaag     240
gaagacaagt catatcaagt aacaagcgtt atttcttctc acaaaaaatg cctgtatcca     300
atcgctacat ttgtccctgg ttcccagccc ggggaattta cccttggcaa catcaagtct     360
tatggtgata agtgtcctta tctggtgaga gttgtctcta ccaattacaa tcagcacgct     420
atggtcttct tcaaacatgc cgatacaaat tacgaaagct tcagtatcac tctgtatgga     480
aggactaaag aattgactag cgagcttaaa gagaacttca tacggttcag caaaagcctg     540
gggctccccg agaaccatat tgtgtttccc gtacctatag atcagtgcat tgacggcagt     600
gcatggtctc accccagtt cgagaaatga                                       630

<210> SEQ ID NO 25
<211> LENGTH: 445
<212> TYPE: PRT
<213> ORGANISM: artificial
<220> FEATURE:
<223> OTHER INFORMATION: secreted anti-CTLA-4 antagonist

<400> SEQUENCE: 25

Met Asp Phe Gln Val Gln Ile Phe Ser Phe Leu Leu Ile Ser Ala Ser
1               5                   10                  15

Val Ile Met Ser Arg Gln Asp Ser Thr Ser Asp Leu Ile Pro Ala Pro
                20                  25                  30

Pro Leu Ser Lys Val Pro Leu Gln Gln Asn Phe Gln Asp Asn Gln Phe
            35                  40                  45

Gln Gly Lys Trp Tyr Val Val Gly Leu Ala Gly Asn Arg Ile Leu Arg
        50                  55                  60

Gln Asp Gln His Pro Met Leu Met Tyr Ala Thr Ile Tyr Glu Leu Lys
65                  70                  75                  80

Glu Asp Lys Ser Tyr Gln Val Thr Ser Val Ile Ser Ser His Lys Lys
                85                  90                  95

```
Cys Leu Tyr Pro Ile Ala Thr Phe Val Pro Gly Ser Gln Pro Gly Glu
            100                 105                 110

Phe Thr Leu Gly Asn Ile Lys Ser Tyr Gly Asp Lys Val Ser Tyr Leu
        115                 120                 125

Val Arg Val Val Ser Thr Asn Tyr Asn Gln His Ala Met Val Phe Phe
130                 135                 140

Lys His Ala Asp Thr Asn Tyr Glu Ser Phe Ser Ile Thr Leu Tyr Gly
145                 150                 155                 160

Arg Thr Lys Glu Leu Thr Ser Glu Leu Lys Glu Asn Phe Ile Arg Phe
                165                 170                 175

Ser Lys Ser Leu Gly Leu Pro Glu Asn His Ile Val Phe Pro Val Pro
            180                 185                 190

Ile Asp Gln Cys Ile Asp Gly Ser Ala Trp Ser His Pro Gln Phe Glu
        195                 200                 205

Lys Asp Pro Ala Glu Pro Lys Ser Pro Asp Lys Thr His Thr Cys Pro
210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
        275                 280                 285

Arg Glu Glu Gln Tyr Asn Ser Thr Tyr Arg Val Val Ser Val Leu Thr
290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
            340                 345                 350

Asp Glu Leu Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys Lys
        435                 440                 445
```

<210> SEQ ID NO 26
<211> LENGTH: 1338
<212> TYPE: DNA
<213> ORGANISM: artificial
<220> FEATURE:
<223> OTHER INFORMATION: nucleotide sequence encoding amino acid
      sequence of SEQ ID NO: 25

-continued

```
<400> SEQUENCE: 26
atggattttc aggtgcaaat cttttctttc cttctgatta gcgcttctgt gatcatgtca      60
aggcaagatt caacttccga tctgatcccg gcgccaccac tctccaaggt accactgcag     120
cagaactttc aggataacca gtttcagggg aaatggtacg tagtgggcct tgccggaaac     180
cgaatcctgc ggcaggatca acccccatg ctgatgtacg ctaccatcta tgagctgaag      240
gaagataaga gttatcaggt gacgagcgtc atctcttccc acaaaaagtg cctgtatccc     300
attgccacat tcgtgccggg cagtcaaccg ggcgagttca ccctcgggaa catcaaatcc     360
tacggcgata aggtaagtta cttggtcagg gtcgtgtcta caactacaa ccaacacgcc      420 atggttttt tcaagcacgc tgatacaaac tacgagagct tctcaatcac cttgtacggt      480
cggaccaaag aactgacgtc tgagcttaag gagaatttta tacgcttctc aaagagcctg     540
gggctgccag aaaaccacat cgttttccca gtgccaatcg accagtgtat cgatggctct     600
gcctggtccc acccacagtt tgagaaagat ccagctgaac caaagagtcc agacaagact     660
cacacatgtc caccttgccc cgccccagaa ttgttgggag gcccctctgt gtttctcttc     720
cctcctaagc caaagacac tctgatgata tcacggaccc cagaggttac ttgcgttgtc      780
gtcgatgtga gtcacgaaga tcctgaggtc aagtttaact ggtacgtaga tggggttgag     840
gtgcataacg caaagaccaa acctcgcgag aacagtata acagtacata tcgcgtggta      900
tccgtgctca ccgtcctcca tcaagactgg ttgaatggaa aggaatacaa gtgcaaagtt     960
tctaacaaag ccctgccagc gcccatcgaa aagactatct ctaaagccaa gggccaacct    1020
cgcgaacctc aagtgtacac ccttcctccc agccgggatg aactgaccaa aaaccaagtg    1080
agcctgacat gtctggtgaa gggtttctat ccctctgata ttgcggttga atgggaaagc    1140
aacggacagc ccgaaaacaa ctacaagact acaccccccg ttttggattc cgatgggagt    1200 ttttttcttgt attctaagct gaccgttgat aaaagtaggt ggcagcaggg caatgtgttt    1260
tcatgtagcg tgatgcacga ggcccttcac aaccactata cccagaagag tcttagcctc    1320
agccctggaa agaagtga                                                   1338

<210> SEQ ID NO 27
<211> LENGTH: 10
<212> TYPE: PRT
<213> ORGANISM: artificial
<220> FEATURE:
<223> OTHER INFORMATION: Strep-tag II

<400> SEQUENCE: 27

Ser Ala Trp Ser His Pro Gln Phe Glu Lys
1               5                   10

<210> SEQ ID NO 28
<211> LENGTH: 188
<212> TYPE: PRT
<213> ORGANISM: artificial
<220> FEATURE:
<223> OTHER INFORMATION: secreted anti-CTLA-4 antagonist without leader
      sequence

<400> SEQUENCE: 28

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30
```

```
Val Val Gly Leu Ala Gly Asn Arg Ile Leu Arg Gln Asp Gln His Pro
            35                  40                  45

Met Leu Met Tyr Ala Thr Ile Tyr Glu Leu Lys Glu Asp Lys Ser Tyr
 50                  55                  60

Gln Val Thr Ser Val Ile Ser Ser His Lys Lys Cys Leu Tyr Pro Ile
 65                  70                  75                  80

Ala Thr Phe Val Pro Gly Ser Gln Pro Gly Glu Phe Thr Leu Gly Asn
                 85                  90                  95

Ile Lys Ser Tyr Gly Asp Lys Val Ser Tyr Leu Val Arg Val Val Ser
                100                 105                 110

Thr Asn Tyr Asn Gln His Ala Met Val Phe Phe Lys His Ala Asp Thr
            115                 120                 125

Asn Tyr Glu Ser Phe Ser Ile Thr Leu Tyr Gly Arg Thr Lys Glu Leu
130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Ser Ala Trp Ser His Pro Gln Phe Glu Lys
            180                 185
```

<210> SEQ ID NO 29
<211> LENGTH: 424
<212> TYPE: PRT
<213> ORGANISM: artificial
<220> FEATURE:
<223> OTHER INFORMATION: secreted anti-CTLA-4 antagonist without leader
      sequence

<400> SEQUENCE: 29

```
Gln Asp Ser Thr Ser Asp Leu Ile Pro Ala Pro Pro Leu Ser Lys Val
 1               5                  10                  15

Pro Leu Gln Gln Asn Phe Gln Asp Asn Gln Phe Gln Gly Lys Trp Tyr
                20                  25                  30

Val Val Gly Leu Ala Gly Asn Arg Ile Leu Arg Gln Asp Gln His Pro
            35                  40                  45

Met Leu Met Tyr Ala Thr Ile Tyr Glu Leu Lys Glu Asp Lys Ser Tyr
 50                  55                  60

Gln Val Thr Ser Val Ile Ser Ser His Lys Lys Cys Leu Tyr Pro Ile
 65                  70                  75                  80

Ala Thr Phe Val Pro Gly Ser Gln Pro Gly Glu Phe Thr Leu Gly Asn
                 85                  90                  95

Ile Lys Ser Tyr Gly Asp Lys Val Ser Tyr Leu Val Arg Val Val Ser
                100                 105                 110

Thr Asn Tyr Asn Gln His Ala Met Val Phe Phe Lys His Ala Asp Thr
            115                 120                 125

Asn Tyr Glu Ser Phe Ser Ile Thr Leu Tyr Gly Arg Thr Lys Glu Leu
130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Ser Ala Trp Ser His Pro Gln Phe Glu Lys Asp Pro Ala Glu
            180                 185                 190

Pro Lys Ser Pro Asp Lys Thr His Thr Cys Pro Pro Cys Pro Ala Pro
195                 200                 205
```

```
Glu Leu Leu Gly Gly Pro Ser Val Phe Leu Phe Pro Lys Pro Lys
210                 215                 220

Asp Thr Leu Met Ile Ser Arg Thr Pro Glu Val Thr Cys Val Val
225                 230                 235                 240

Asp Val Ser His Glu Asp Pro Glu Val Lys Phe Asn Trp Tyr Val
            245                 250                 255

Asp Gly Val Glu Val His Asn Ala Lys Thr Lys Pro Arg Glu Glu Gln Tyr
        260                 265                 270

Asn Ser Thr Tyr Arg Val Val Ser Val Leu Thr Val Leu His Gln Asp
        275                 280                 285

Trp Leu Asn Gly Lys Glu Tyr Lys Cys Lys Val Ser Asn Lys Ala Leu
290                 295                 300

Pro Ala Pro Ile Glu Lys Thr Ile Ser Lys Ala Lys Gly Gln Pro Arg
305                 310                 315                 320

Glu Pro Gln Val Tyr Thr Leu Pro Pro Ser Arg Asp Glu Leu Thr Lys
                325                 330                 335

Asn Gln Val Ser Leu Thr Cys Leu Val Lys Gly Phe Tyr Pro Ser Asp
            340                 345                 350

Ile Ala Val Glu Trp Glu Ser Asn Gly Gln Pro Glu Asn Asn Tyr Lys
        355                 360                 365

Thr Thr Pro Pro Val Leu Asp Ser Asp Gly Ser Phe Phe Leu Tyr Ser
370                 375                 380

Lys Leu Thr Val Asp Lys Ser Arg Trp Gln Gln Gly Asn Val Phe Ser
385                 390                 395                 400

Cys Ser Val Met His Glu Ala Leu His Asn His Tyr Thr Gln Lys Ser
                405                 410                 415

Leu Ser Leu Ser Pro Gly Lys Lys
            420

<210> SEQ ID NO 30
<211> LENGTH: 178
<212> TYPE: PRT
<213> ORGANISM: human

<400> SEQUENCE: 30

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
                20                  25                  30

Val Val Gly Leu Ala Gly Asn Ala Ile Leu Arg Glu Asp Lys Asp Pro
            35                  40                  45

Gln Lys Met Tyr Ala Thr Ile Tyr Glu Leu Lys Glu Asp Lys Ser Tyr
        50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
        115                 120                 125

Asn Arg Glu Tyr Phe Lys Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160
```

```
Leu Pro Glu Asn His Ile Val Phe Pro Val Pro Ile Asp Gln Cys Ile
            165                 170                 175

Asp Gly
```